(12) United States Patent
Sato et al.

(10) Patent No.: US 11,866,054 B2
(45) Date of Patent: Jan. 9, 2024

(54) MANAGEMENT ASSISTANCE SYSTEM

(71) Applicant: LOGISTEED, LTD., Tokyo (JP)

(72) Inventors: Kiminori Sato, Tokyo (JP); Hideaki Nagumo, Tokyo (JP)

(73) Assignee: LOGISTEED, LTD., Tokyo (JP)

( * ) Notice: Subject to any disclaimer, the term of this patent is extended or adjusted under 35 U.S.C. 154(b) by 120 days.

(21) Appl. No.: 16/968,525

(22) PCT Filed: Jan. 11, 2019

(86) PCT No.: PCT/JP2019/000674
§ 371 (c)(1),
(2) Date: Aug. 7, 2020

(87) PCT Pub. No.: WO2019/155818
PCT Pub. Date: Aug. 15, 2019

(65) Prior Publication Data
US 2021/0039653 A1    Feb. 11, 2021

(30) Foreign Application Priority Data
Feb. 9, 2018 (JP) .................. 2018-021653

(51) Int. Cl.
*B60W 40/08* (2012.01)
*B60W 50/14* (2020.01)
*G07C 5/00* (2006.01)

(52) U.S. Cl.
CPC ............ *B60W 40/08* (2013.01); *B60W 50/14* (2013.01); *G07C 5/008* (2013.01); *B60W 2040/0818* (2013.01); *B60W 2540/221* (2020.02)

(58) Field of Classification Search
CPC ............... B60W 40/08; B60W 50/14; B60W 2040/0818; B60W 2540/221; G07C 5/008;
(Continued)

(56) References Cited

U.S. PATENT DOCUMENTS

2004/0054468 A1    3/2004  Yamada et al.
2010/0030434 A1    2/2010  Okabe et al.
(Continued)

FOREIGN PATENT DOCUMENTS

JP    2003/130662 A    5/2003
JP    2006/023937 A    1/2006
(Continued)

OTHER PUBLICATIONS

Japanese Office Action dated Nov. 7, 2019 for Application No. 2018-021653, 8 pages.
(Continued)

*Primary Examiner* — James J Yang
(74) *Attorney, Agent, or Firm* — Knobbe, Martens, Olson & Bear, LLP

(57) ABSTRACT

A management assistance system includes a first monitoring device for monitoring a travel state of a target vehicle, a second monitoring device for monitoring a physical state during driving of a driver, a server, and a manager terminal. The first monitoring device transmits first monitoring information to the server when the travel state satisfies a prescribed first warning condition, and the second monitoring device transmits second monitoring information to the server when the physical state during driving satisfies a prescribed second warning condition. The server includes a determination processing unit for determining whether or not a monitoring-required determination condition based on the first monitoring information and the second monitoring information; and a transmission unit for transmitting monitoring-required notification information indicating that the driving situation of the driver reaches the monitoring-required level to the manager terminal, when the determination processing unit determines that the monitoring-required determination condition is satisfied.

20 Claims, 15 Drawing Sheets

(58) Field of Classification Search
CPC ....... G07C 5/0841; A61B 5/0245; A61B 5/16; A61B 5/18; G08B 21/00; G08B 21/06; G08G 1/00; G08G 1/16
See application file for complete search history.

(56) References Cited

U.S. PATENT DOCUMENTS

| | | | |
|---|---|---|---|
| 2013/0073122 A1 | 3/2013 | Hoyshiya | |
| 2017/0274907 A1* | 9/2017 | Palmer | B60W 50/14 |
| 2018/0365998 A1* | 12/2018 | Shibata | G08G 1/096791 |

FOREIGN PATENT DOCUMENTS

| | | | |
|---|---|---|---|
| JP | 2007203913 A | | 8/2007 |
| JP | 2008/123448 A | | 5/2008 |
| JP | 2008/296682 A | | 12/2008 |
| JP | 2013065246 A | | 4/2013 |
| JP | 2014027961 A | | 2/2014 |
| JP | 2014123287 A | | 7/2014 |
| JP | 2016/081079 A | | 5/2016 |
| JP | 2017027414 A | | 2/2017 |
| JP | 6132327 B1 | | 5/2017 |

OTHER PUBLICATIONS

International Search Report dated Mar. 12, 2019 for PCT/JP2019/000674, 4 pages.
Chinese Office Action dated Jan. 20, 2022 for Chinese Patent Application No. 201980012501.2.
International Preliminary Report on Patentability dated Aug. 20, 2020 for Application No. PCT/JP2019/000674, 10 pages.
Japanese Office Action dated Jul. 15, 2021 for Japanese Patent Application No. 2020-003463. 9 pages including translation.
Sep. 16, 2022 $2^{nd}$ Chinese Office Action from related CN 201980012501.2 (14 pgs).
Decision of Rejection received in Chinese Application No. 201980012501.2, dated May 8, 2023.

* cited by examiner

Fig. 3

| Determination Value | Determination Content | Content |
|---|---|---|
| 1-1 | Left Lane Departure Warning | Detect When Crossing to Left Side of Lane Without Turning On Turn Indicator While Traveling at Higher Than or Equal to Predetermined Speed Per Hour |
| 1-2 | Right Lane Departure Warning | Detect When Crossing to Right Side of Lane Without Turning on Turn Indicator While Traveling at Higher Than or Equal to Predetermined Speed Per Hour |
| 1-3 | Distance With Front Vehicle Warning | Notify When Number of Seconds to Reach Point Where Front Vehicle Was at Becomes Constant When Continued to Travel at Same Vehicle Speed |
| 1-4 | Low-Speed Front Vehicle Collision Warning | Detect When Falling within Virtual Bumper Range Set in Advance at Time of Low-Speed Traveling |
| 1-5 | Front Vehicle Collision Warning | Monitor Front Vehicle and Detect When Determining that there is Risk of Colliding within A Predetermined Second from Relative Speed, Relative Acceleration, Etc. |
| 1-6 | Pedestrian Collision Warning | Detect When Collision to Pedestrian in Front is Predicted During Traveling |
| 2-1 | Acceleration: Small Risk | Detect When Occurrence of G in One of Up, Down, Left, Right, Front, and Back is Relatively Small |
| 2-2 | Acceleration: Medium Risk | Detect When Occurrence of G in One of Up, Down, Left, Right, Front, and Back is Large to Certain Extent |
| 2-3 | Acceleration: Large Risk | Detect When Occurrence of G in One of Up, Down, Left, Right, Front, and Back is Extremely Large |

Fig. 5

| Determination Value | Determination Content | Content |
|---|---|---|
| 3-0 | Seating Not Confirmed | Detect When Data Cannot be Measured |
| 3-1 | Sympathetic Nerve Enhanced State | Detect When Driver 2 is in Excited State |
| 3-2 | Normal Determination | Detect When Driver 2 is not or Barely Tired |
| 3-3 | Attention Determination | Detect When Driver 2 is likely to Get Sleepy |
| 3-4 | Attention Determination | Detect When Driver 2 Feels Fatigue |
| 3-5 | Warning Determination | Detect When Driver 2 is Sleepy |
| 3-6 | Warning Determination | Detect Indication of Driver 2 to Fall Asleep |
| 3-7 | Emergency Warning Determination | Awakening Reducing State of Driver 2 Cannot be Detected |
| 3-8 | Emergency Warning Determination | Detect When Driver 2 is in Urgent Sleep State or Sleep State. |

Fig. 6

| Condition No. | Condition | Monitoring Target Occurrence Time Interval | Target Item (1) | Target Item (2) | Target Item (3) | Target Item (4) |
|---|---|---|---|---|---|---|
| 1 | At Least One of Items is Satisfied | 10 Minutes | (d1) Determination Value 1-6: One or More Times | (d1) Determination Value 1-5: 10 or More Times | (d1) Determination Value 2-3: 2 or More Times | (d1) Determination Value 3-8: 5 or More Times |
| 2 | All Items are Satisfied | 30 Minutes | (d1) Any of Determination Values 1-1, 1-2, 1-5: 30 or More Times | (d1) Any of Determination Values 2-2, 2-3:100 or More Times | | |
| 3 | All Items are Satisfied | 30 Minutes | (d1) Any of Determination Values 1-1, 1-2, 1-5: 30 or More Times | (d2) Any of Determination Values 3-5, 3-6, 3-7, 3-8: 10 or More Times | | |
| 4 | All Items are Satisfied | 30 Minutes | (d1) Any of Determination Values 2-2, 2-3:100 or More Times | (d2) Any of Determination Values 3-5, 3-6, 3-7, 3-8: 10 or More Times | | |

Fig. 13

| | LF/HF < 0.8 | 0.8 < LF/HF < 2.0 | 2.0 < LF/HF < 5.0 | 5.0 < LF/HF |
|---|---|---|---|---|
| 57 < Ti | Good | Good | Attention | Caution |
| 42 < Ti < 57 | Good | Good | Attention | Caution |
| 37 < Ti < 42 | Attention | Attention | Attention | Caution |

Ti: Deviation Value
LF: Index Reflecting Sympathetic Nerve
HF: Index Reflecting Parasympathetic Nerve

Fig. 14

| Condition No. | Condition | Monitoring Target Occurrence Time Interval | Target Item (1) | Target Item (2) | Target Item (3) | Target Item (4) |
|---|---|---|---|---|---|---|
| 1 | At Least One of Items is Satisfied | 10 Minutes | (d1) Determination Value 1-6 : One or More Times | (d1) Determination Value 1-5 : 10 or More Times | (d1) Determination Value 2-3 : 2 or More Times | (d1) Determination Value 3-8 : 5 or More Times |
| 2 | All Items are Satisfied | 30 Minutes | (d1) Any of Determination Values 1-1, 1-2, 1-5: 30 or More Times | (d1) Any of Determination Values 2-2, 2-3:100 or More Times | | |
| 3 | All Items are Satisfied | 30 Minutes | (d1) Any of Determination Values 1-1, 1-2, 1-5: 30 or More Times | (d2) Any of Determination Values 3-5, 3-6, 3-7, 3-8: 10 or More Times | | |
| 4 | All Items are Satisfied | 30 Minutes | (d1) Any of Determination Values 2-2, 2-3:100 or More Times | (d2) Any of Determination Values 3-5, 3-6, 3-7, 3-8: 10 or More Times | | |
| 5 | At Least One of Items is Satisfied | 10 Minutes | (d1) Any of Determination Values 1-1, 1-2, 1-3, 1-4, 1-5, 1-6 : $n_1$ or More Times | (d1) Any Of Determination Values 2-2, 2-3: $n_2$ or More Times | (d2) Any of Determination Values 3-5, 3-6, 3-7, 3-8: $n_3$ or More Times | |

MANAGEMENT ASSISTANCE SYSTEM

TECHNICAL FIELD

The present invention relates to a management assistance system that assists management of a driving situation of a driver who drives a target vehicle.

BACKGROUND ART

Conventionally, there is a device that when a biological signal of a driver is acquired in real time and when the biological signal is examined and analyzed and determination is made that the physical state is not suitable for driving, a break is encouraged or an alarm is generated to wake the driver. As such a device, one that senses a pulse wave and makes the determination (see Patent Document 1 below), one that makes the determination from information related to heart rate, blood pressure, and autonomic nerves (see Patent Document 2 below), and the like are known.

PRIOR ART DOCUMENT

Patent Document

Patent Document 1: JP-B2-6132327
Patent Document 2: JP-A-2014-27961

SUMMARY OF THE INVENTION

Problems to be Solved by the Invention

The fatigue and drowsiness of driver greatly affect the driving situation. Generally, a driver is encouraged to stop the vehicle and take a break when feeling tired or drowsy in order to drive safely.

On the other hand, since the driver is also a human being, the driver may become overconfident on his/her physical condition and continue to drive due to geographical environmental factors such as the destination point, which is the destination of transportation, and the break point scheduled in advance approaching, and psychological environmental factors such as the driver desiring to deliver the package to the destination point as soon as possible. In such a case, if each of the devices described above is mounted on the vehicle, the physical condition of the driver can be objectively known by the notification of the warning sound, and the warning sound can act as an incentive to take a break.

The carrier owns a plurality of vehicles and employs a large number of drivers. From the viewpoint of safety management, the carrier often desires to manage the driving situation of each driver. However, each of the devices described above is developed only for the purpose of making the driver conscious by issuing a warning sound in each vehicle. That is, even if these devices are mounted on each vehicle, the driving situation of each driver in a distant place cannot be managed.

With advancement in IoT technology of recent years, technologies enabling communication between devices have been developed in various fields. In view of such, the inventors of the present invention first considered providing a separate communication means with respect to a device for monitoring the biological signal of the driver during driving as described in the patent document described above, and installing a function to transmit warning information to the server when a warning sound is notified from the device to the vehicle.

With such a configuration, the manager can know that the physical condition of each driver is deteriorating by accessing the server. Furthermore, since the manager can recognize the deterioration of the physical condition of the driver, the driver can be verbally instructed to take a break by using, for example, a mobile phone. Thus, the driver can be forced to take a break, and the effect of preventing an accident beforehand is expected.

However, in a carrier that employs a large number of drivers, the number of drivers to be managed by the manager becomes inevitably large. In this case, the manager needs to keep monitoring the server, which arises a problem that the work load imposed on the manager increases.

With respect to such a problem, there is considered a method of causing the server to transmit information to the manager's terminal at a time point when the server receives the warning information transmitted from the device mounted on the vehicle. Specifically, consideration is made to adopt a mechanism in which an alert is notified to terminals such as smartphones and personal computers owned by the manager. However, even with such a method, in a case of a carrier employing an extremely large number of drivers, notifications are expected to be made at high frequency to the terminal of the manager, but there still exists a problem that a high work load will be imposed on the manager.

The inventors of the present invention found, through intensive researches, that one of the backgrounds of such a problem is that the characteristics of the device itself that detects a biological signal and monitors the physical condition of the driver described above is involved. That is, the device described above is generally configured to generate a warning sound when the biological signal of the driver deviates, even slightly, from the value set as the value at normal time from the viewpoint of preventing in advance an accident at the time of driving as much as possible. Therefore, even in a state where a warning sound is issued from the detected biological signal, the health condition of the driver may actually be as good as the normal time. This also involves the fact that there is an individual difference in the correlation between the information detected by the biological signal and the physical condition of the actual driver.

Therefore, if a communication means is provided on the device described above and a function of transmitting to the server the information that the warning sound has been generated from the device is installed, the frequency that the information is notified to the terminal of the manager who manages a large number of drivers increases. Furthermore, as described above, even when the signal indicating that the warning sound has been issued is notified, a case where there is no problem in the physical condition of the actual driver is included, and hence whether or not the driver is in a driving situation genuinely requiring monitoring cannot be recognized. However, there is a reason that a big accident must be prevented beforehand. In other words, when the above system is operated, the manager is required to monitor a large number of drivers simultaneously based on the information notified in large amounts, which again imposes a high work load on the manager.

In view of the above problems, the present invention provides a management assistance system that causes a manager to intensively monitor a driver when the driver is in a driving situation genuinely requiring monitoring.

Means for Solving the Problems

The present invention relates to a management assistance system that assists management of a driving situation of a driver who drives a target vehicle, the management assistance system including, a first monitoring device that is mounted on the target vehicle to monitor a travel state of the target vehicle;

a second monitoring device that is mounted on the target vehicle to monitor a physical state during driving of the driver;

a server configured to wirelessly communicate with the first monitoring device and the second monitoring device; and a manager terminal configured to wirelessly communicate with the server, wherein when the travel state satisfies a prescribed first warning condition, the first monitoring device outputs a first warning signal to the target vehicle and transmits first monitoring information corresponding to the travel state to the server together with identification information for identifying the target vehicle or the driver serving as a transmitting source;

when the physical state during driving satisfies a prescribed second warning condition, the second monitoring device outputs a second warning signal to the target vehicle and transmits second monitoring information corresponding to the physical state during driving to the server together with the identification information; and the server includes, a receiving unit that receives the first monitoring information transmitted from the first monitoring device and the second monitoring information transmitted from the second monitoring device, a storage unit that stores a monitoring-required determination condition for determining whether or not a driving situation of the driver reaches a monitoring-required level, a determination processing unit that determines whether or not the monitoring-required determination condition is satisfied based on the first monitoring information and the second monitoring information received by the receiving unit, and a transmitting unit that, when the determination processing unit determines that the monitoring-required determination condition is satisfied, transmits monitoring-required notification information indicating that the driving situation of the driver reaches a monitoring-required level to the manager terminal together with the identification information.

In the present specification, the "manager" does not necessarily have to be a legal "operation manager", but refers to a person who has an operation authority for the "manager terminal".

The management assistance system determines whether or not the driving situation of the driver reaches a monitoring-required level based on the information transmitted from the first monitoring device and the second monitoring device mounted on the target vehicle. The first monitoring device is a device that monitors the travel state of the target vehicle. The second monitoring device is a device that monitors the physical state during driving of the driver.

The first monitoring device outputs a first warning signal to the target vehicle when the travel state of the target vehicle satisfies a prescribed first warning condition. For example, when sudden brake is applied on the target vehicle or when the separation distance between the target vehicle and a front obstacle (vehicle, pedestrian, etc.) becomes extremely short, the first monitoring device detects these situations and outputs the first warning signal in the vehicle. The first warning signal may be a warning sound emitted from a speaker or the like, or may be character or image information displayed at a position visible by the driver such as a meter panel or a navigation screen. Furthermore, the vibrator may be provided on a seat on which the driver sits to give vibration. In this case, the vibration signal corresponds to the first warning signal. The driver recognizes that he/she has been driving such that the travel state satisfies the first warning condition by recognizing the first warning signal. As a result, the effect as a motivation for safe driving is exhibited.

The second monitoring device outputs a second warning signal to the target vehicle when the physical state during driving of the driver satisfies a prescribed second warning condition. For example, the second monitoring device outputs a second warning signal in the vehicle when detecting that the driver is in a sleepy or fatigue state. Similar to the first warning signal, the second warning signal may be a warning sound emitted from a speaker or the like, or may be character or image information displayed at a position visible by the driver such as a meter panel or a navigation screen. Furthermore, the vibrator may be provided on a seat on which the driver sits to give vibration. The driver recognizes that he/she is feeling sleepy or tired by recognizing the second warning signal. As a result, the effect of awakening the driver's consciousness is exhibited.

When detecting that the travel state satisfies the first warning condition, the first monitoring device transmits information (first monitoring information) corresponding to the travel state to the server together with the identification information. Similarly, when detecting that the physical state during driving satisfies the second warning condition, the second monitoring device transmits information corresponding to the physical state during driving (second monitoring information) to the server together with the identification information. In the determination processing unit, the server determines whether or not the driving situation of the driver is the required monitoring level based on the first monitoring information and the second monitoring information transmitted from each device.

It is assumed that the first monitoring device and the second monitoring device are set with strict warning conditions (first warning condition, second warning condition) for the purpose of ensuring driving safety.

For example, with the first monitoring device, when another vehicle suddenly cuts in from the adjacent lane, detection may be made that the inter-vehicle distance has reduced and determination may be made that the first warning condition is satisfied. That is, although there is no particular problem with the driving situation of the driver, there are cases where the travel state satisfies the first warning condition by the influence of the travel state of the other vehicle. Therefore, whether the driver is feeling fatigue or sleepy is difficult to genuinely determine based only on the monitoring result of the first monitoring device.

The second monitoring device is a device that monitors the physical state during driving, and as one example, monitors the physical state during driving based on the biological signal of the driver. However, the correlation between the value indicated by the biological signal of the driver and the actual physical condition of the driver varies from driver to driver. Therefore, whether the driver is feeling fatigue or sleepy is difficult to genuinely determine based only on the monitoring result of the second monitoring device.

The server included in the management assistance system according to the present invention includes a storage unit, and the storage unit stores in advance a monitoring-required determination condition for determining whether or not the driving situation is the monitoring-required level based on the first monitoring information transmitted from the first monitoring device and the second monitoring information transmitted from the second monitoring device. When the travel state of the target vehicle and the physical state during driving of the driver satisfy certain conditions, consideration is made that the driving situation is not good and that an accident may occur. As an example, this corresponds to a case where the first monitoring device detects that a large change in acceleration has occurred a great number of times within a prescribed time, and the second monitoring device detects that the driver is in a state in which the driver is likely to fall asleep over a plurality of times within the prescribed time.

The server included in the management assistance system according to the present invention transmits, only when the driving situation of the driver is determined to reach the monitoring-required level based on the first monitoring information and the second monitoring information, the monitoring-required notification information indicating the same to the manager terminal. That is, according to the management assistance system of the present invention, in a case where a warning condition is set for each of the first monitoring device and the second monitoring device, and a situation occurs in which a warning is notified from each device, notification to the manager terminal is not carried out unless determination is made that the monitoring with respect to the driver is genuinely necessary. As a result, the manager only needs to pay attention to the driver associated with the monitoring-required notification information as the monitoring target only when the monitoring-required notification information from the server is notified to the manager terminal, which reduces the burden on the manager.

Each of the first monitoring device and the second monitoring device has a function of outputting a warning signal to the vehicle independently from each device. Therefore, even when the first monitoring device or the second monitoring device is mounted alone in the vehicle, there is a certain degree of effect of making the driver be aware of safe driving. However, as described above, each device generally has a condition for outputting a warning signal strictly set so as to maximally exhibit the function of preventing an accident when the device is mounted alone. In such a case, the warning signal may be frequently output in the vehicle even though the driver himself/herself has no problem regarding the physical condition. If such a state continues, the driver becomes accustomed to the warning signal being output in the vehicle, and the significance of the warning signal decreases.

On the other hand, as described above, according to the management assistance system according to the present invention, when it is determined that the monitoring with respect to the driver is genuinely necessary, this determination is automatically notified to the manager terminal. When detecting that such notification is made, the manager can confirm the current physical condition or the like to the driver by using means such as a mobile phone or wireless communication. In other words, even if the driver is accustomed to the warning signal from the first monitoring device or the second monitoring device mounted on the vehicle, such confirmation contact is made from the manager only when the monitoring is genuinely necessary, and thus the driver can re-recognize that his/her physical condition is not so good and can be motivated to take a break.

More specifically, the first monitoring information includes information converted into numerical values according to risk of the travel state;

the second monitoring information includes information converted into numerical values according to non-awakening degree of the driver;

when receiving the first monitoring information and the second monitoring information, the receiving unit stores the identification information, which is a transmitting source, time information related to received date and time, and the first monitoring information and the second monitoring information in the storage unit;

the monitoring-required determination condition includes information related to monitoring target occurrence time interval and number of occurrence threshold value defined according to the risk and the non-awakening degree;

the determination processing unit can determine that the monitoring-required determination condition is satisfied when the number of occurrences of the risk described in the first monitoring information or the non-awakening degree described in the second monitoring information within the monitoring target occurrence time interval exceeds the number of occurrence threshold value based on the first monitoring information, the second monitoring information, and the time information stored in the storage unit.

For example, when the driver feels sleepy or fatigue, the frequency of occurrence of a specific travel state such as sudden braking, sudden acceleration, and sudden steering tends to increase. In addition, when the driver feels sleepy or fatigue, the frequency at which the second monitoring device determines that the physical state during driving of the driver is a state of high non-awakening degree based on the biological signal of the driver increases. That is, according to the management assistance system, when a state indicating high risk and/or high non-awakening degree is detected at a high frequency within a limited time, the server determines that the driving situation of the driver is genuinely a monitoring-required level and the notification indicating the same is automatically made to the manager terminal.

More specifically, the first monitoring device can detect at least one of a separation distance between the target vehicle and a front obstacle (vehicle, pedestrian, etc.) located in front of the target vehicle, whether the target vehicle departed from a lane in which the target vehicle is traveling, and an acceleration of the target vehicle, determines the risk set in advance based on the detection result; and the second monitoring device can detect at least one of a heartbeat and a pulse wave of the driver, and determine the non-awakening degree set in advanced based on the detection result.

The storage unit may store the monitoring-required determination condition corresponding to the identification information.

As described above, there may be individual differences in the correlation between the information obtained from the second monitoring device and the genuine physical condition (sleepiness, fatigue) of the actual driver. Furthermore, there may be individual differences in the correlation between the information obtained from the first monitoring device and the risk of the actual travel state, depending on the number of driving years, driving technique, and the like of the driver. According to the configuration described above, the monitoring-required determination condition that takes into consideration the individual characteristics of each driver can be set, so that the accuracy of determining whether or not the driving situation of the driver reaches the monitoring-required level can be further improved.

Furthermore, the storage unit may store information on a pre-driving physical state, which is a physical state before driving the target vehicle, of the driver, in association with the identification information; and the server may include a correction processing unit that corrects the monitoring-required determination condition based on the pre-driving physical state for each driver.

For example, when the body temperature of the driver is slightly higher than the normal temperature in a state before driving, it is assumed that the driver is more likely to be fatigued than in normal times. Furthermore, for example, when the state of autonomic nerve of the driver is not preferable in a state before driving, it is assumed that the driver may more easily feel sleepy than in normal times and may tend to drive aimlessly. In such a case, for example, the correction processing unit corrects the monitoring-required determination condition of the driver so as to be stricter than usual. As a result, since notification is made to the manager terminal even in a case where the monitoring-required notification information is not normally notified to the manager terminal, the manager can intensively monitor the driver.

The management assistance system may include a traveling road determination device that is mounted on the target vehicle and that, at a time point where a road on which the target vehicle is traveling is changed from a general road to a highway and a time point where the road is changed from a highway to a general road, transmits information indicating the change to the server together with the information related to the changed time; and the storage unit may store the monitoring-required determination condition that differs depending on whether the road on which the target vehicle is travelling is the general road or the highway.

The form of driving situation and how fatigue is felt are different between when driving on a general road and when driving on a highway. According to the configuration described above, the monitoring-required determination condition can be switched according to the form of each road, and hence the accuracy in determining whether or not the driving situation of the driver is the monitoring-required level can be further improved. As the traveling road determination device, for example, an automatic payment system (ETC) mounted on the target vehicle can be used.

The management assistance system may include a position information detection device that is mounted on the target vehicle and that detects current position information of the target vehicle and transmits the position information to the server, where when the first monitoring information or the second monitoring information is received by the receiving unit, the server may store the position information of the target vehicle at the time of reception in the storage unit together with each monitoring information, and when the determination processing unit determines that the monitoring-required determination condition is satisfied, the transmitting unit may transmit the monitoring-required notification information to the manager terminal together with the identification information and the position information.

According to the configuration described above, the manager can recognize the current position of the driver based on the position information displayed on the manager terminal. Therefore, for example, an appropriate break point existing near the position information can be contacted to the driver. As the position information detection device, for example, a car navigation system mounted on the target vehicle can be used.

Effect of the Invention

According to the management assistance system of the present invention, the manager can be assisted to intensively monitor the driver when the driver is in a driving situation genuinely requiring monitoring.

BRIEF DESCRIPTION OF THE DRAWINGS

FIG. 3 is a table showing a correspondence relationship between an example of a first warning condition and information converted into numerical values according to the risk of the travel state related to each condition.

FIG. 5 is a table showing a correspondence relationship between an example of a physical state during driving specified by a determination unit based on various biological signals of a driver and a determination value corresponding to each state.

FIG. 6 is a table showing an example of the monitoring-required determination condition stored in a storage unit provided in the server.

FIG. 13 is an example of an index when evaluating the state of the autonomic nerve.

FIG. 14 is a table showing an example of a monitoring-required determination condition that takes into consideration the pre-driving physical state stored in a storage unit included in the server.

MODE FOR CARRYING OUT THE INVENTION

First Embodiment

A first embodiment of a management assistance system according to the present invention will be described with reference to the drawings. This management assistance system is used for the purpose of assisting the management of the driving situation of the driver who drives the target vehicle.

Figure 1:
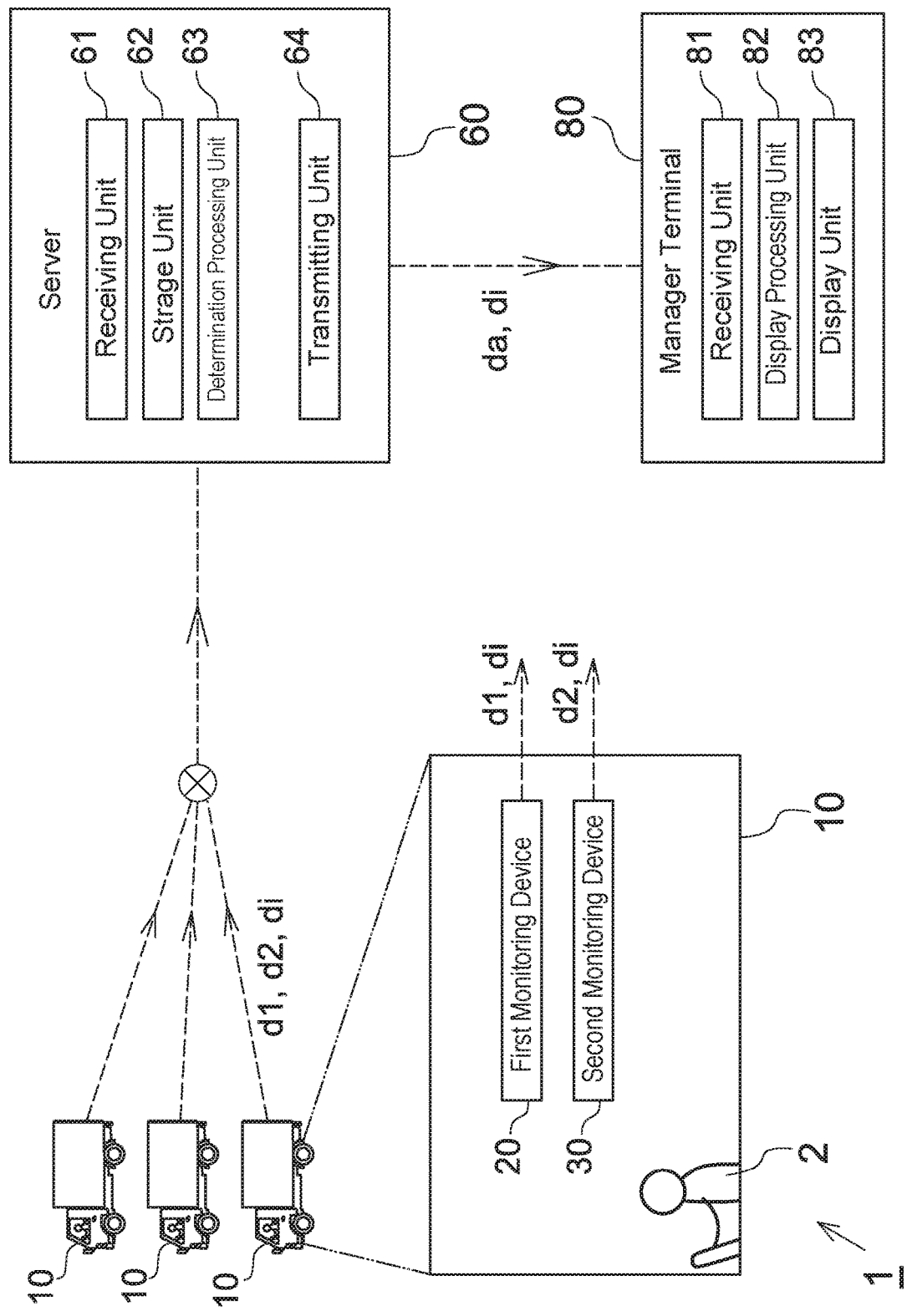
FIG. 1 is a block diagram schematically showing the configuration of a first embodiment of a management assistance system of the present invention.

FIG. 1 is a block diagram schematically showing the overall configuration of the management assistance system. A management assistance system 1 includes a target vehicle 10, a server 60, and a manager terminal 80.

<Target Vehicle 10>

The target vehicle 10 is a vehicle to be driven by a driver 2. In the present embodiment, a case where the target vehicle 10 is a truck for transporting cargo will be described as an example, but the target vehicle may be other vehicles such as buses and taxis as long as the target vehicle is a vehicle used in an application in which the driver 2 drives and travels between a plurality of points.

The target vehicle 10 includes a first monitoring device 20 and a second monitoring device 30 mounted in the vehicle. The first monitoring device 20 and the second monitoring device 30 are both configured to wirelessly communicate with the server 60. The format of this communication is not limited, and for example, Wi-Fi (registered trademark), the Internet, or the like can be used.

(First Monitoring Device 20)

Figure 2:
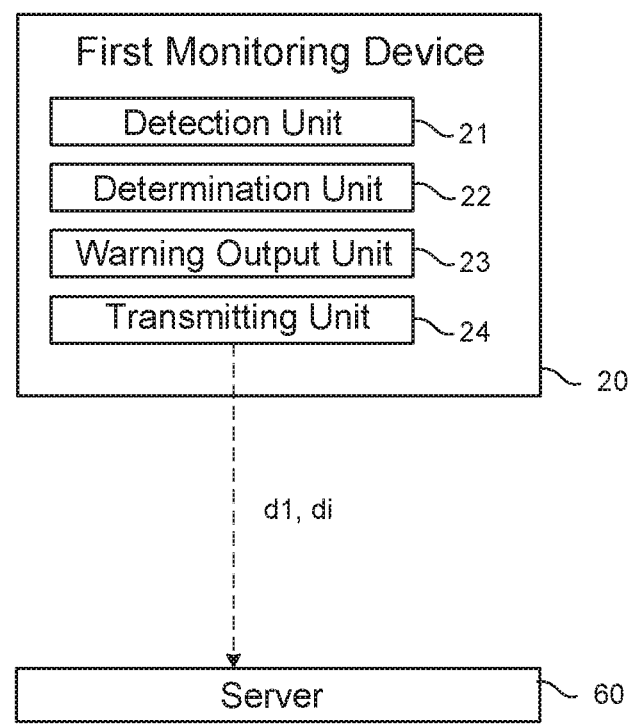
FIG. 2 is a block diagram schematically showing an internal configuration of a first monitoring device.

The first monitoring device 20 is a device that monitors the travel state of the target vehicle 10. More specifically, as shown in FIG. 2, the first monitoring device 20 includes a detection unit 21 that detects the travel state of the target vehicle 10, a determination unit 22 that determines whether or not the travel state of the target vehicle 10 satisfies a prescribed warning condition based on the result detected by the detection unit 21, a warning output unit 23 that outputs a warning signal, and a transmitting unit 24 that transmits prescribed information to a server.

The detection unit 21 includes an acceleration sensor that detects the acceleration of the target vehicle 10 and an imaging sensor that detects a separation distance from a front obstacle (vehicle, pedestrian, etc.) and/or a lane departure condition. Furthermore, the first monitoring device 20 may include a speed sensor that detects the speed of the target vehicle 10. Some of these sensors may be configured by sensors mounted on the target vehicle 10 itself.

The determination unit 22 is a calculation processing unit that determines whether or not the travel state of the target vehicle 10 satisfies a prescribed warning condition (hereinafter referred to as "first warning condition") based on various information of the target vehicle 10 detected by the detection unit 21, and is configured by dedicated software and/or hardware. The first warning condition is stored in advance in a storage unit (not shown) in the first monitoring device 20.

FIG. 3 is a table showing a correspondence relationship between an example of the first warning condition and information converted into numerical values according to the risk of the travel state related to each condition. Note that in FIGS. 3 and 5 described later, the determination value is expressed as "m-n" (m and n are both numbers), where the former "m" indicates the type of device (sensor) from which the data was acquired and the latter "n" indicates the risk by being replaced with a numerical value. The device from which the data is acquired corresponds to the first monitoring device 20 or the second monitoring device 30, and/or the acceleration sensor or the imaging sensor in the first monitoring device 20. The notation method of the determination value is an example, and the present invention is not limited to thereto.

(1) When the detection unit 21 detects that the target vehicle 10 has crossed the lane without turning on the turn indicator while the target vehicle 10 is traveling at higher than or equal to a prescribed speed (e.g., higher than or equal to 55 km/hour), the determination unit 22 sets a determination value 1-1 (left lane) or a determination value 1-2 (right lane) with respect to the travel state.

(2) When determining that the number of seconds to reach the point where the vehicle in front was at is less than or equal to a prescribed value (e.g., less than or equal to three seconds) at the time the target vehicle 10 continues to travel at the same vehicle speed based on the information detected by the detection unit 21, the determination unit 22 sets a determination value 1-3 with respect to the travel state.

(3) When determining that a vehicle body of the target vehicle 10 falls within a virtual bumper range set in advance while the target vehicle 10 is traveling at a low speed (e.g., less than or equal to 30 km/hour) based on the information detected by the detection unit 21, the determination unit 22 sets a determination value 1-4 with respect to the travel state.

(4) When determining that there is a risk of colliding with the vehicle in front within a prescribed second (e.g. 2.5 seconds) at the time the target vehicle 10 continues to travel at the same vehicle speed based on the information detected by the detection unit 21, the determination unit 22 sets a determination value 1-5 with respect to the travel state.

(5) When determining that there is a risk of the target vehicle 10 colliding with a pedestrian in front during traveling based on the information detected by the detection unit 21, the determination unit 22 sets a determination value 1-6 with respect to the travel state.

(6) Based on the change in acceleration detected by the detection unit 21, the determination unit 22 sets a determination value 2-1 (small risk), 2-2 (medium risk), and 2-3 (large risk) with respect to the travel state according to the magnitude of G generated in the target vehicle 10. The determination value 2-3 is the driving of highest risk. In this determination, the determination unit 22 may detect the timing at which the engine started and exclude the change in acceleration at the relevant timing from the first warning condition. The determination value 2-1 may be excluded from the first warning condition.

When the determination unit 22 determines that the travel state of the target vehicle 10 satisfies the condition (first warning condition) as shown in the above example, the first monitoring device 20 outputs a warning signal (first warning signal) from the warning output unit 23 into the target vehicle 10. Furthermore, at this time, the first monitoring device 20 transmits information indicating the travel state of the target vehicle 10 at the relevant time point (first monitoring information d1), together with the identification information di of the driver 2, from the transmitting unit 24 to the server 60.

The warning output unit 23 is means for generating and outputting a corresponding audio signal, character or image signal, and is configured by dedicated software and/or hardware. The transmitting unit 24 is means for converting the first monitoring information d1 into transmission data associated with the identification information di of the driver 2 based on the information determined by the determination unit 22, and then transmitting the transmission data to the server 60 through wireless communication, and is configured by dedicated software and/or hardware.

The first warning signal merely needs to be a form recognizable by the driver 2, and for example, may be an audio signal output from a speaker mounted on the first monitoring device 20 or the target vehicle 10, or may be a character or image signal output on a screen mounted on the first monitoring device 20 or the target vehicle 10. As another example, a vibration signal from a vibrator output to a seat on which the driver 2 sits may be used. Furthermore, when the first monitoring device 20 and the smartphone owned by the driver 2 are configured to be communicable, an audio signal, a character/image signal may be output to the smartphone of the driver 2.

In this case, the first warning signal may include information indicating the content of the warning. For example, when it is determined as the travel state corresponding to the determination value 1-1 by the first monitoring device 20, an audio signal indicating that the target vehicle 10 has deviated the lane with respect to the left side may be output from the speaker, or character information or image information indicating that the target vehicle 10 has deviated the lane with respect to the left side may be displayed on the screen.

The driver 2 recognizes that he/she has been driving such that the travel state satisfies the first warning condition by recognizing the audio and character/image information corresponding to the first warning signal in the target vehicle 10. Thus, the driver 2 is urged to pay attention to the subsequent driving.

The first monitoring information d1 transmitted from the first monitoring device 20 to the server 60 includes the content of the corresponding warning. As an example, the first monitoring information d1 includes the determination values shown in FIG. 3.

Furthermore, as described above, the first monitoring information d1, together with the identification information di for identifying the driver 2, is transmitted from the first monitoring device 20 to the server 60. The first monitoring device 20 may, for example, store information for identifying the mounted target vehicle 10 (vehicle number etc.), or store information of the driver 2 (employee ID etc.). In the former case, the number of the target vehicle 10 may be described as the identification information di, and, for example, a table in which the correspondence status of the target vehicle 10 and the driver 2 at the current time point is described in advance may be stored in the server 60. In the latter case, the employee ID of the driver 2 is described as the identification information di. In this case, before the driver 2 gets onto the target vehicle 10, a process of temporarily storing the employee ID of the driver 2 in advance in the first monitoring device 20 may be performed.
(Second Monitoring Device 30)

Figure 4:
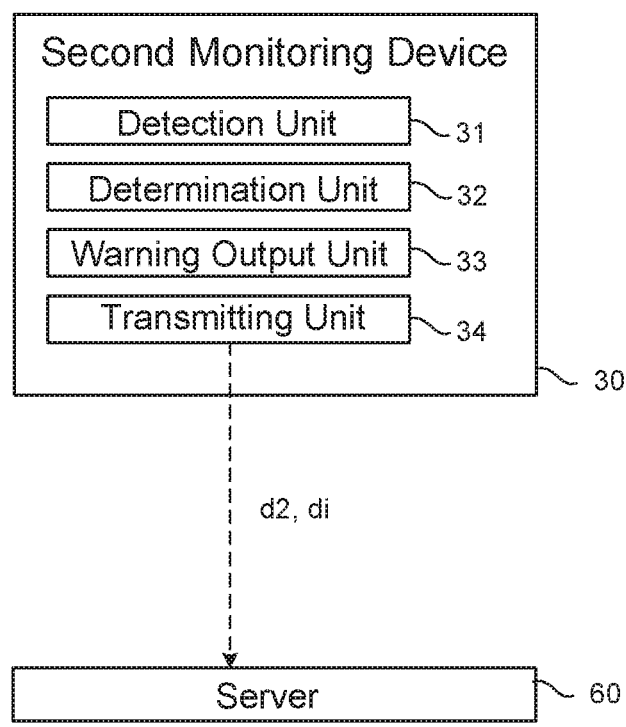
FIG. 4 is a block diagram schematically showing an internal configuration of a second monitoring device.

The second monitoring device 30 is a device that monitors the physical state during driving of the driver 2. More specifically, as shown in FIG. 4, the second monitoring device 30 includes a detection unit 31 that detects the physical state during driving of the driver 2, a determination unit 32 that determines whether or not the physical state during driving of the driver 2 satisfies a prescribed warning condition based on the result detected by the detection unit 31, a warning output unit 33 that outputs a warning signal, and a transmitting unit 34 that transmits prescribed information to a server.

The detection unit 31 is formed by, for example, a sensor provided on a seat on which the driver 2 sits, and detects biological signals such as the heartbeat and pulse wave of the driver 2. A pressure sensor can be used as an example.

The determination unit 32 is a calculation processing unit that specifies a physical state during driving of the driver 2 and determines whether or not the specified physical state during driving satisfies a prescribed warning condition (hereinafter referred to as "second warning condition") based on various biological signals of the driver 2 detected by the detection unit 31, and is configured by dedicated software and/or hardware. The second warning condition is stored in advance in a storage unit (not shown) in the second monitoring device 30.

FIG. 5 shows a correspondence relationship between an example of a physical state during driving specified by the determination unit 32 based on various biological signals of the driver 2 and determination values corresponding to each state.

(1) When determining that the seating of the driver 2 cannot be confirmed based on the information of the biological signal detected by the detection unit 31, the determination unit 32 sets a determination value 3-0 with respect to the physical state during driving of the driver 2. This setting is not necessary.

(2) Based on the information of the biological signal detected by the detection unit 31, the determination unit 32 sets a determination value 3-1 with respect to the physical state during driving of the driver 2 when determining that the sympathetic nerve of the driver 2 is enhanced and the driver is in an excited state, and sets a determination value 3-2 with respect to the physical state during driving of the driver 2 when determining that driver 2 is not or barely tired. The determination values 3-1 and 3-2 correspond to the state in which the non-awakening degree of the driver 2 is low (awakening degree is high).

(3) Based on the information of the biological signal detected by the detection unit 31, the determination unit 32 sets a determination value 3-3 with respect to the physical state during driving of the driver 2 when determining as a state in which driver 2 is likely to get sleepy, and sets a determination value 3-4 with respect to the physical state during driving of the driver 2 when determining as a state in which driver 2 feels fatigue. The determination values 3-3 and 3-4 correspond to a state in which the non-awakening degree of the driver 2 is not so low (awakening degree is not so high).

(4) Based on the information of the biological signal detected by the detection unit 31, the determination unit 32 sets a determination value 3-5 with respect to the physical state during driving of the driver 2 when determining as a state in which the driver 2 is sleepy, and sets a determination value 3-6 with respect to the physical state during driving of the driver 2 when determining as a state in which indication to fall asleep of the driver 2 is detected. The determination values 3-5 and 3-6 correspond to the state in which the non-awakening degree of the driver 2 is high (awakening degree is low).

(5) Based on the information of the biological signal detected by the detection unit 31, the determination unit 32 sets a determination value 3-7 with respect to the physical state during driving of the driver 2 when determining that the driver 2 cannot detect the awakening degree reducing state (awakening degree reducing state), and sets a determination value 3-8 with respect to the physical state during driving of the driver 2 when determining that the driver 2 is in an urgent sleep state or reliably in a sleep state. The determination values 3-7 and 3-8 correspond to the state in which the non-awakening degree of the driver 2 is extremely high (awakening degree is extremely low).

In the present embodiment, when the determination unit 32 determines that the determination value corresponding to the physical state during driving of the driver 2 is 3-3 to 3-8, the warning output unit 33 outputs a warning signal (second warning signal) to the target vehicle 10. That is, in this embodiment, the second warning condition is set to whether the physical state during driving of the driver 2 is 3-3 to 3-8. Furthermore, at this time, the second monitoring device 30 transmits information indicating the physical state during driving of the driver 2 at this time point (second monitoring information d2), together with the identification information di of the driver 2, from the transmitting unit 34 to the server 60.

The warning output unit 33 is means for generating and outputting a corresponding audio signal, character or image signal, and is configured by dedicated software means and/or hardware means. The transmitting unit 34 is means for converting the second monitoring information d2 into transmission data associated with the identification information di of the driver 2 based on the information determined by the determination unit 32, and then transmitting the transmission data to the server 60 through wireless communication, and is configured by dedicated software means and/or hardware means.

The second warning signal merely needs to be a form recognizable by the driver 2, and for example, may be an audio signal output from a speaker mounted on the second monitoring device 30 or the target vehicle 10, or may be a character or image signal output on a screen mounted on the second monitoring device 30 or the target vehicle 10. Furthermore, when the second monitoring device 30 and the smartphone owned by the driver 2 are configured to be communicable, an audio signal, a character/image signal may be output to the smartphone of the driver 2.

At that time, the second warning signal may include information indicating the content of the warning. For example, when determined as the travel state corresponding to the determination value 3-7 by the second monitoring device 30, an audio signal indicating that the driver 2 is feeling sleepy may be output from the speaker, or character information or image information indicating that the driver 2 is feeling sleepy may be displayed on the screen.

The driver 2 recognizes audio and character/image information corresponding to the second warning signal in the target vehicle 10 to recognize that he/she is feeling sleepy or tired, and the conscious is awakened. Thus, for example, the driver 2 is urged to voluntarily take a break.

The second monitoring information d2 transmitted from the second monitoring device 30 to the server 60 includes the content of the corresponding warning. As an example, the second monitoring information d2 includes each determination value shown in FIG. 5.

Furthermore, as described above, the second monitoring information d2, together with the identification information di for identifying the driver 2, is transmitted from the second monitoring device 30 to the server 60. The second monitoring device 30 may, for example, store information for identifying the mounted target vehicle 10 (vehicle number etc.), or store information of the driver 2 (employee ID etc.).

In a case where each warning signal is formed by an audio signal, the warning signal output from the first monitoring device 20 and the warning signal output from the second monitoring device 30 may be emitted from the same speaker. Similarly, in a case where each warning signal is formed by a character or image signal, the warning signal output from the first monitoring device 20 and the warning signal output from the second monitoring device 30 may be displayed on the same screen.

<Server 60>

As shown in FIG. 1, in the present embodiment, the server 60 includes a receiving unit 61, a storage unit 62, a determination processing unit 63, and a transmitting unit 64. The receiving unit 61 is processing means having a function of converting the data received through the telecommunication line into a form in which the data can be calculated, and the transmitting unit 64 is processing means that converts the data to a prescribed form in which transmission and reception is possible, and transmits the data through the telecommunication line. The determination processing unit 63 is a calculation processing unit that performs prescribed signal processing (calculation) based on the acquired information, and is configured by dedicated software and/or hardware. The storage unit 62 is formed of a storage medium such as a flash memory or a hard disk.

Upon receiving the first monitoring information d1 transmitted from the first monitoring device 20 and the second monitoring information d2 transmitted from the second monitoring device 30, the receiving unit 61 causes the storage unit 62 to store the information therein. At this time, as described above, since each of the first monitoring information d1 and the second monitoring information d2 is associated with the identification information di for identifying the driver 2, these monitoring information (d1, d2) are stored in the storage unit 62 for each identification information di. Furthermore, the date and time received by the receiving unit 61 or the date and time when each monitoring information (d1, d2) is transmitted from the target vehicle 10 are also stored. In the latter case, when the transmitting unit 24 of the first monitoring device 20 transmits the first monitoring information d1, or when the transmitting unit 34 of the second monitoring device 30 transmits the second monitoring information d2, a process of describing information related to the transmission date and time with respect to each monitoring information (d1, d2) can be performed.

The determination processing unit 63 determines whether or not a prescribed determination condition (hereinafter also referred to as "monitoring-required determination condition") is satisfied based on each monitoring information (d1, d2) for each driver 2 stored (accumulated) in the storage unit 62. The information related to the monitoring-required determination condition is stored in the storage unit 62 in advance.

FIG. 6 is a table showing an example of the monitoring-required determination condition. When confirming that the first monitoring information d1 or the second monitoring information d2 is received by the receiving unit 61, the determination processing unit 63 detects the content of the first monitoring information d1 or the second monitoring information d2 associated with the identification information di of the driver 2 and the number of receiving times before a prescribed time defined in advance with the receiving time as a starting point with respect to the storage unit 62.

In the example shown in FIG. 6, the following contents are stored in the storage unit 62 as the monitoring-required determination conditions. In this example, the monitoring-required determination condition includes information related to a monitoring target occurrence time interval (e.g., 10 minutes, 30 minutes or the like) and a number of occurrence threshold value (e.g., 10 times, 100 times or the like) defined in advance in accordance with the first monitoring information d1 and the second monitoring information d2. Furthermore, in this example, the monitoring information (d1, d2) corresponding to each determination value corresponds to the example shown in FIG. 3 or 5.

(1) Condition 1: One of the following conditions is satisfied.

The server 60 has received the first monitoring information d1 indicating the determination value 1-6 at least once within the past 10 minutes including the current time.

The server 60 has received the first monitoring information d1 indicating the determination value 1-5 10 or more times within the past 10 minutes including the current time.

The server 60 has received the first monitoring information d1 indicating the determination value 2-3 two or more times within the past 10 minutes including the current time.

The server 60 has received the second monitoring information d2 indicating the determination value 3-8 five or more times within the past 10 minutes including the current time.

(2) Condition 2: All of the following conditions are satisfied.

The server 60 has received the first monitoring information d1 indicating the determination value 1-1, 1-2, or 1-5 30 or more times within the past 30 minutes including the current time.

The server 60 has received the first monitoring information d1 indicating the determination value 2-2 or 2-3 100 or more times within the past 30 minutes including the current time.

(3) Condition 3: All of the following conditions are satisfied.

The server 60 has received the first monitoring information d1 indicating the determination value 1-1, 1-2, or 1-5 30 or more times within the past 30 minutes including the current time.

The server 60 has received the second monitoring information d2 indicating the determination value 3-5, 3-6, 3-7, or 3-8 10 or more times within the past 30 minutes including the current time.

(4) Condition 4: All of the following conditions are satisfied.

The server 60 has received the first monitoring information d1 indicating the determination value 2-2 or 2-3 100 or more times within the past 30 minutes including the current time.

The server 60 has received the second monitoring information d2 indicating the determination value 3-5, 3-6, 3-7, or 3-8 10 or more times within the past 30 minutes including the current time.

When confirming that the monitoring-required determination condition described above is satisfied, the determination processing unit 63 creates information indicating that the driving situation of the driver 2 reaches a monitoring-required level (hereinafter referred to as "monitoring-required notification information da"). The transmitting unit 64 transmits the monitoring-required notification information da to the manager terminal 80 together with the identification information di of the driver 2.

<Manager Terminal 80>

The manager terminal 80 is not limited to that mode as long as the manager terminal is a device configured to communicate with the server 60, and for example, is configured by a general-purpose device such as a smartphone, a tablet PC, a notebook PC, a desktop PC, or the like, or a dedicated terminal related to the management assistance system 1. When the manager terminal 80 is a general-purpose device, a dedicated application program to adapt to the operation of the management assistance system 1 may be installed. The manager terminal 80 may be stored at a position spaced apart from the installing location of the server 60, or may be held (carried) by the manager.

The manager terminal 80 includes a receiving unit 81 that receives the monitoring-required notification information da transmitted from the transmitting unit 64 of the server 60, a display processing unit 82 that creates information for display based on the received monitoring-required notification information da, and a display unit 83 that displays the information created by the display processing unit 82. The receiving unit 81 is processing means having a function of converting the data received through the telecommunication line into a form in which the data can be calculated. The display processing unit 82 is a calculation processing unit that performs prescribed signal processing (calculation) based on the acquired information, and is configured by dedicated software and/or hardware. The display unit 83 corresponds to the monitor screen. For example, as in the case where the manager terminal 80 is configured by a smartphone, the display unit 83 and the manager terminal 80 may be configured integrally, or as in the case where the manager terminal 80 is configured by a desktop PC, the display unit 83 and the manager terminal 80 may be separately configured.

Figure 7:
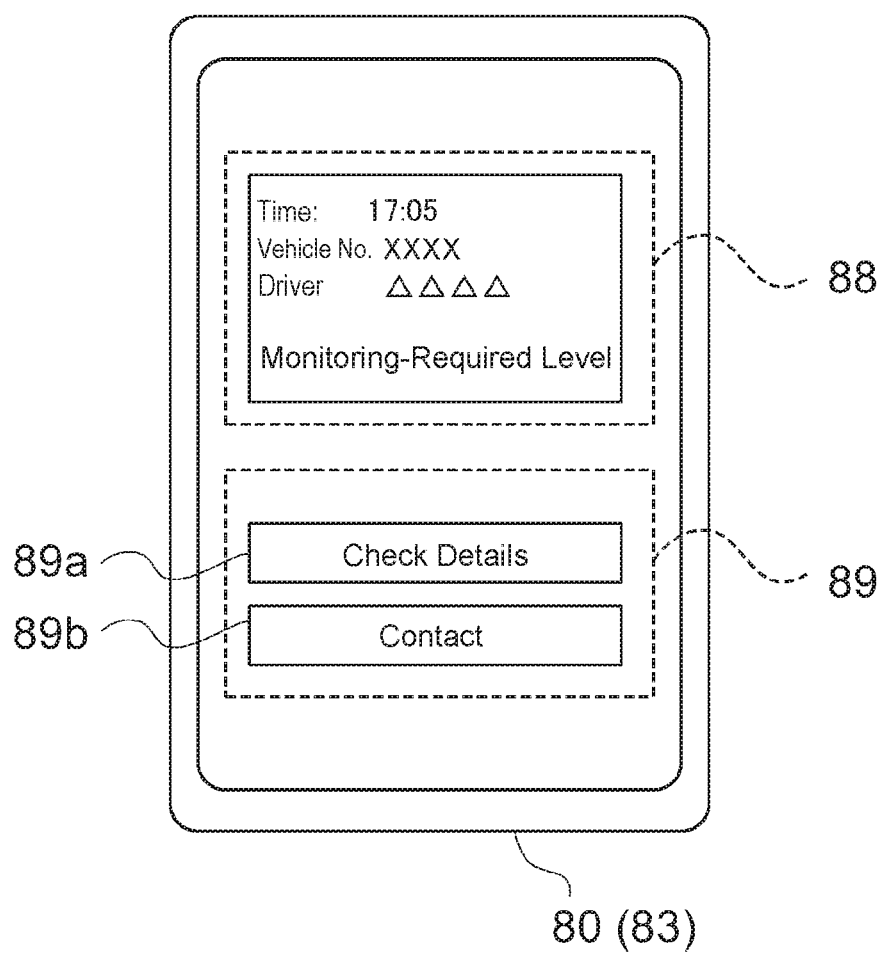
FIG. 7 is an example of a screen displayed on the manager terminal that has monitoring-required notification information.

FIG. 7 is an example of a screen displayed on the manager terminal 80 that has the monitoring-required notification information da. In the example shown in FIG. 7, the display unit 83 displays a message display region 88 and an operation region 89.

In the message display region 88, information for specifying the target driver 2 and the target vehicle 10 and information indicating as reaching the monitoring-required level are displayed. Furthermore, in the operation region 89, operation buttons (89*a*, 89*b*, . . . ) that can be operated by the manager are displayed. In this example, an operation button 89*a* for viewing in detail the content of the monitoring-required notification information da notified this time and an operation button 89*b* for contacting the target driver 2 are displayed.

For example, when the manager operates the operation button 89*a*, the manager terminal 80 transmits an instruction signal for acquiring target information from the transmitting unit (not shown) to the server 60. When receiving the instruction signal, the server 60 transmits, for example, each monitoring information (d1, d2) within a latest prescribed time of the target driver 2 from the storage unit 62 to the manager terminal 80 and causes the display unit 83 of the manager terminal 80 to display the information. Thus, the manager can recognize what kind of driving situation the target driver 2 was in the latest.

Furthermore, when the information regarding the work plan is stored for each driver 2 in the storage unit 62 of the server 60, the information is transmitted from the server 60 to the manager terminal 80. For example, the time of the monitoring-required notification information da notified this time is collated with the information regarding the work plan, and, for example, the display unit 83 of the manager terminal 80 can be caused to display the fact of currently advancing from point A to point B.

When the manager operates the operation button 89*b*, the manager terminal 80 can contact the mobile phone of the driver 2 or the wireless communication device mounted on the target vehicle 10 which the driver 2 is driving. In this case, the manager terminal 80 may have a call function and a message transmitting function as needed. Thus, the manager can directly verbally convey the words calling attention to the driver 2, and can prevent an accident. Furthermore, the manager terminal 80 may transmit character information that calls attention to the mobile phone of the driver 2 or the target vehicle 10 which the driver 2 is driving.

<Flowchart>

Figure 8:
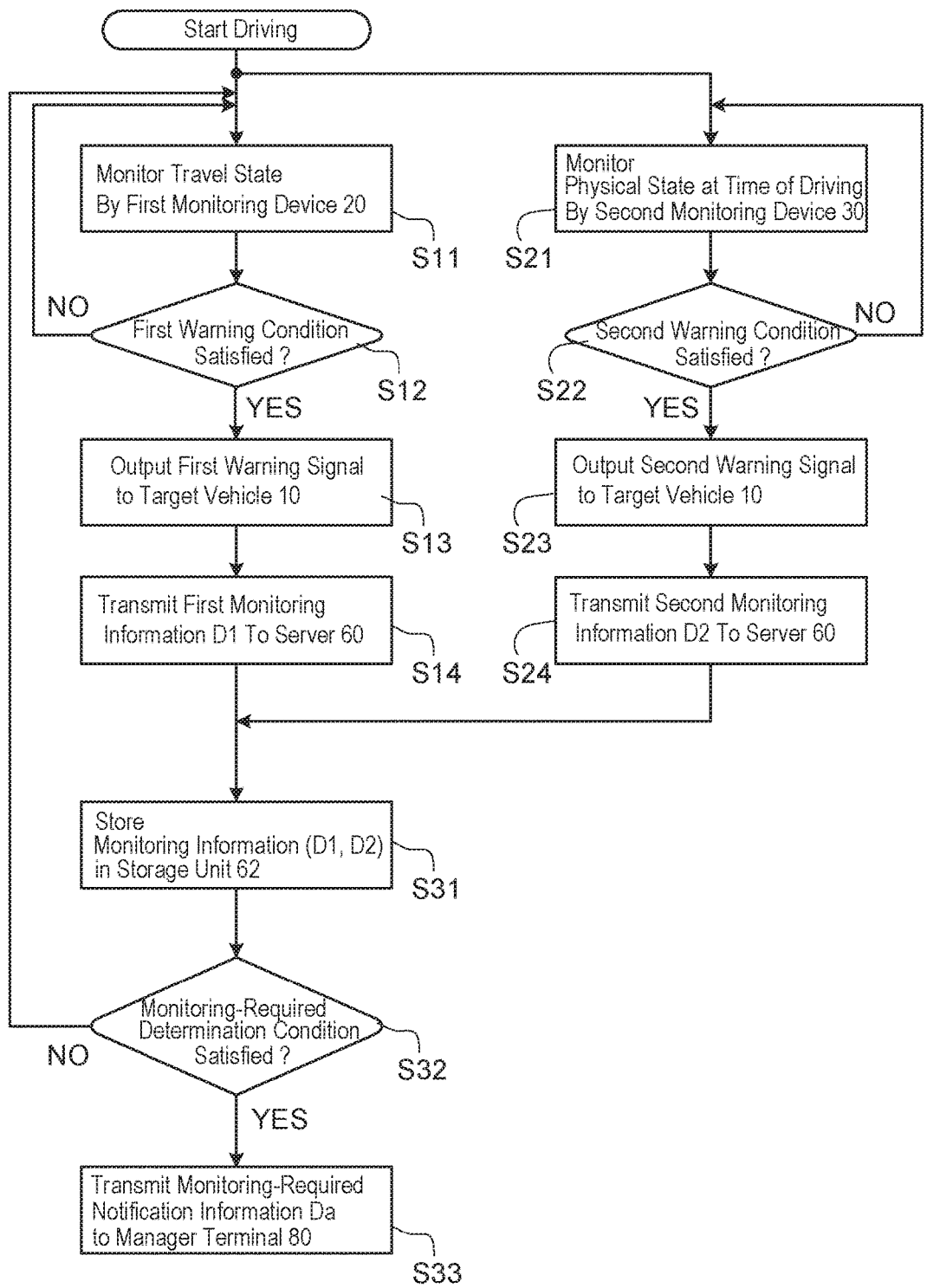
FIG. 8 is a flowchart schematically showing a processing flow of the management assistance system according to the first embodiment.

FIG. 8 is a flowchart schematically showing the processing flow of the management assistance system 1 of the present embodiment. Since the contents are redundant, the description will be simplified.

While the target vehicle 10 is traveling, the first monitoring device 20 monitors the travel state of the target vehicle 10 (step S11), and the second monitoring device 30 monitors the physical state during driving of the driver 2 (step S21). These monitoring may be constantly performed when the target vehicle 10 is traveling.

When determining that the travel state of the target vehicle 10 satisfies the first warning condition described above (YES in step S12), the first monitoring device 20 outputs a first warning signal into the target vehicle 10 (step S13), and transmits the first monitoring information d1 indicating the travel state of the target vehicle 10 at this time point to the server 60 (step S14).

When determining that the travel state of the target vehicle 10 satisfies the second warning condition (YES in step S22), the second monitoring device 30 outputs a second warning signal into the target vehicle 10 (step S23), and transmits the second monitoring information d2 indicating the physical state during driving of the driver 2 at this time point to the server 60 (step S24).

When receiving each monitoring information (d1, d2), the server 60 causes the storage unit 62 to store the information therein (step S31). Then, whether or not the monitoring-required determination condition is satisfied is determined based on each monitoring information (d1, d2) for each driver 2 stored in the storage unit 62 in the determination processing unit 63 (step S32). When the monitoring-required determination condition is satisfied (YES in step S32), the monitoring-required notification information da indicating that the driving situation of the driver 2 reaches the monitoring-required level is transmitted to the manager terminal 80 (step S33).

According to the configuration described above, only when it is determined as being at the monitoring-required level based on the past travel state of the target vehicle 10 and the physical state during driving of the driver 2 by the server 60, a notification indicating the same is made to the manager terminal 80. As a result, the management burden on the manager is reduced as compared with a case where the manager confirms each time a warning is issued from the monitoring device (20, 30) mounted on the target vehicle 10.

As described above, the management assistance system 1 combines the information based on the travel state of the target vehicle 10 and the information based on the physical state of the driver 2 to determine whether or not the driving situation reaches the monitoring-required level. Therefore, according to the management assistance system 1, the accuracy of determining whether or not the risk is high is improved. Thus, when the management assistance system 1 is operated, the driver 2 can recognize that the driver is actually in a dangerous state due to the direct contact from the manager.

That is, according to the management assistance system 1, a notification is made from the server 60 to the manager not in a state where each device (20, 30) mounted on the target vehicle 10 simply outputs a warning signal, but only in a more dangerous state (state in which an accident is likely to occur). Thus, the direct contact from the manager to the driver 2 means that the driver 2 is in a state in which an accident is likely to occur. In other words, when the driver 2 receives a direct contact from the manager, the driver 2 is caused to recognize he/she has been driving in a state in which an accident is likely to occur, and can at least be temporarily woken and strongly encouraged to immediately take a break in an appropriate place nearby.

It should be noted that the monitoring-required determination conditions stored in the storage unit 62 of the server 60 may be set according to the driver 2. The physical state during driving of the driver 2 monitored by the second monitoring device 30 is monitored based on the biological signal of the driver 2. However, since there are individual differences in the biological signal, it is assumed that the content indicated by the determination value determined by the second monitoring device 30 and the actual physical state of the driver 2 do not necessarily match.

Furthermore, depending on the number of driving years, driving technique and the like of the driver 2, it is assumed that the content indicated by the determination value determined by the first monitoring device 20 and the actual risk of the target vehicle 10 do not necessarily match.

Therefore, in consideration of the tendency of the biological signal of each driver 2, the driving technique, and the like in advance, the monitoring-required determination conditions can be set for each driver 2 and stored in the storage unit 62 of the server 60. For example, in the conditions illustrated in FIG. 6, the monitoring target occurrence time interval and the number of occurrence threshold value can be changed, or the condition of combination of the first monitoring information d1 and the second monitoring information d2 can be changed according to the driver 2.

Figure 9:
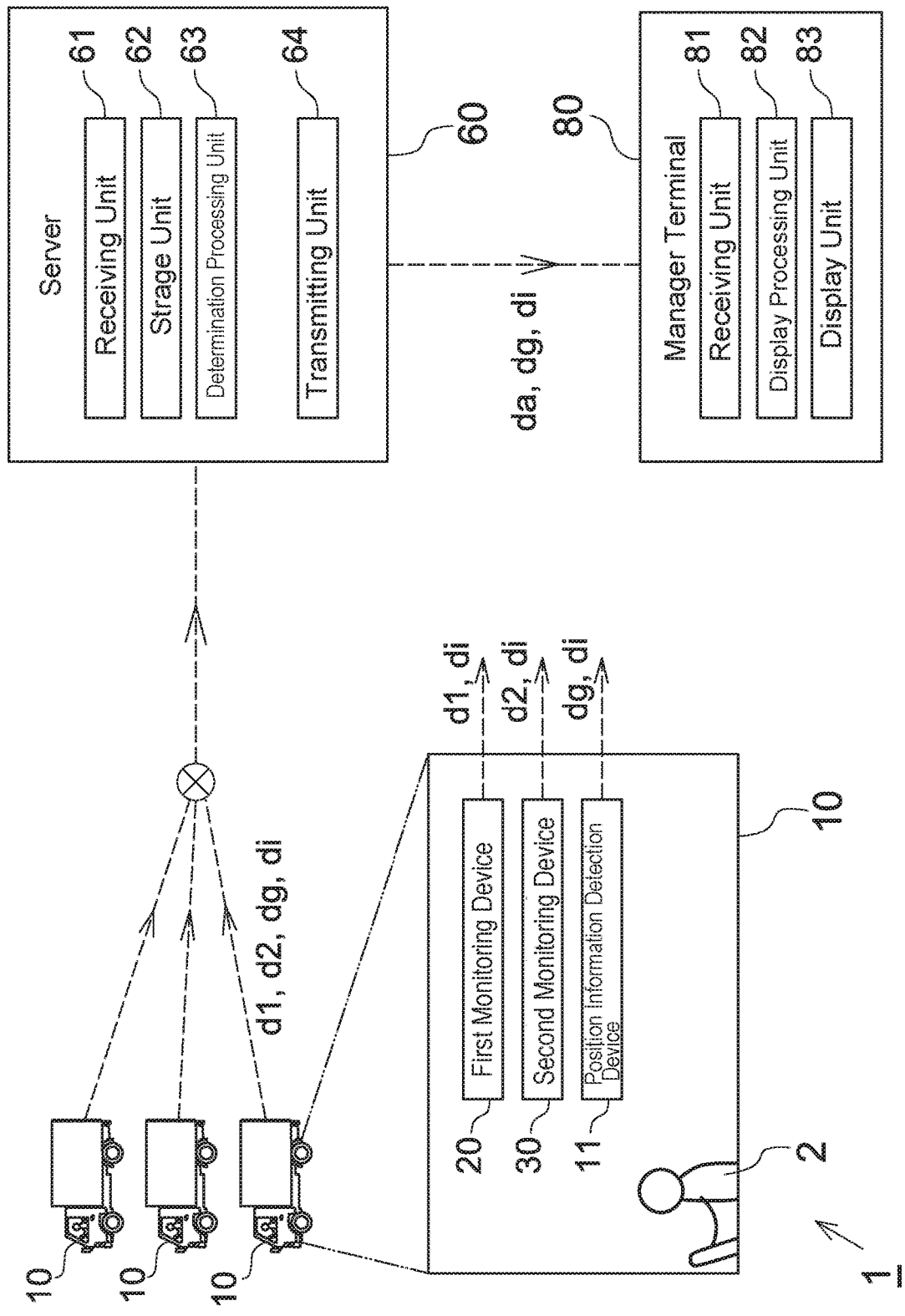
FIG. 9 is another block diagram schematically showing the configuration of the first embodiment of the management assistance system according to the present invention.

Another Configuration Example (1) As shown in FIG. 9, in a case where the target vehicle 10 includes a position information detection device 11 that detects the current position information of the target vehicle 10, the position information dg of the target vehicle 10 at a time point when each monitoring information (d1, d2) is transmitted from each monitoring device (20, 30) to the server 60 may also be transmitted. The position information detection device 11 is, for example, a car navigation system mounted on the target vehicle 10. According to this configuration, the position information dg of the target vehicle 10 at a time point when each warning condition is satisfied can be stored in the storage unit 62 of the server 60 in association with each monitoring information (d1, d2).

The position information dg may be transmitted from the position information detection device 11 to each monitoring device (20, 30), and then transmitted from each monitoring device (20, 30) to the server 60 together with each monitoring information (d1, d2). Alternatively, as another method, the position information dg may be transmitted from the position information detection device 11 to the server 60 at a time point when each monitoring information (d1, d2) is transmitted from each monitoring device (20, 30) to the server 60.

Furthermore, as another method, the position information detection device 11 may periodically transmit the position information dg to the server 60 at a prescribed time interval. In this case, the server 60 may store the position information dg in the storage unit 62 and also read out the position information dg transmitted at the closest time from the storage unit 62 at a time point when the server receives each monitoring information (d1, d2) transmitted from each monitoring device (20, 30).

In step S32, when determining that the monitoring-required determination condition is satisfied based on each monitoring information (d1, d2) for each driver 2 (YES in step S32), the determination processing unit 63 transmits, to the manager terminal 80, the monitoring-required notification information da indicating that the driving situation of the driver 2 is the monitoring-required level, together with the identification information di of the driver 2 and the position information dg.

Figure 10:
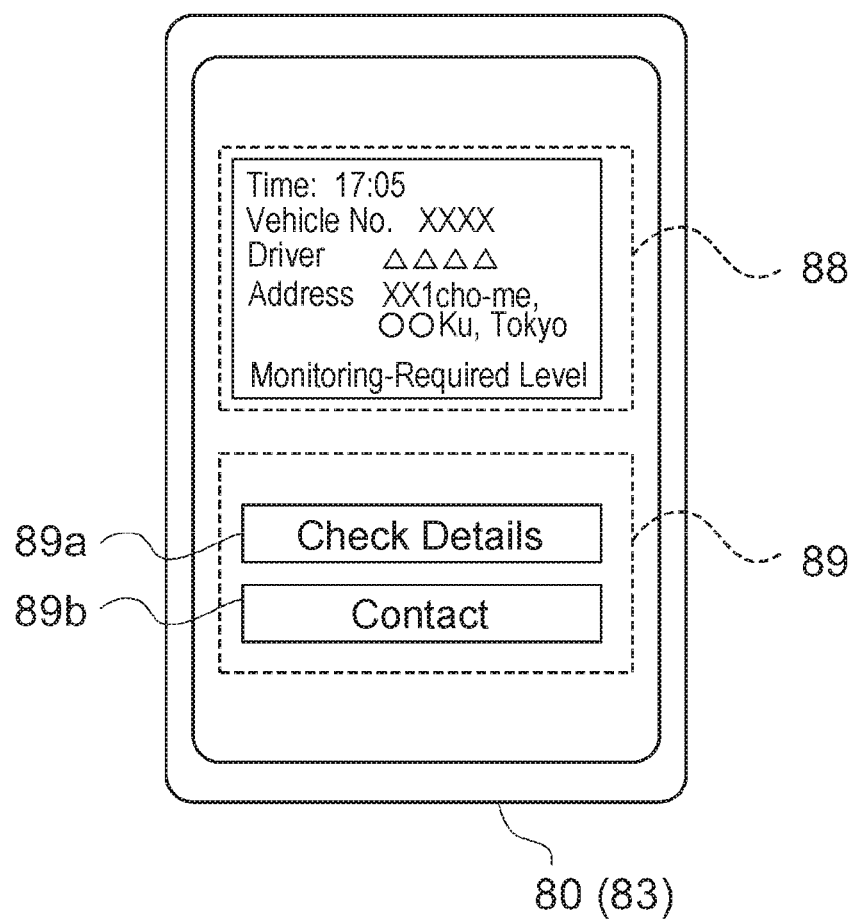
FIG. 10 is another example of the screen displayed on the manager terminal that received the monitoring-required notification information.

FIG. 10 is an example of a screen displayed on the manager terminal 80 that received the monitoring-required notification information da together with the position information dg. In the example shown in FIG. 10, information regarding the position of the target vehicle 10 is simply shown in the message display region 88. In this case, when the manager operates the operation button 89a, detailed information regarding the current position of the driver 2 can be displayed on the display unit 83 of the manager terminal 80. Based on this information, the manager can detect an appropriate rest area near the current position of the target vehicle 10 and notify the driver 2 of the same.

Figure 11:
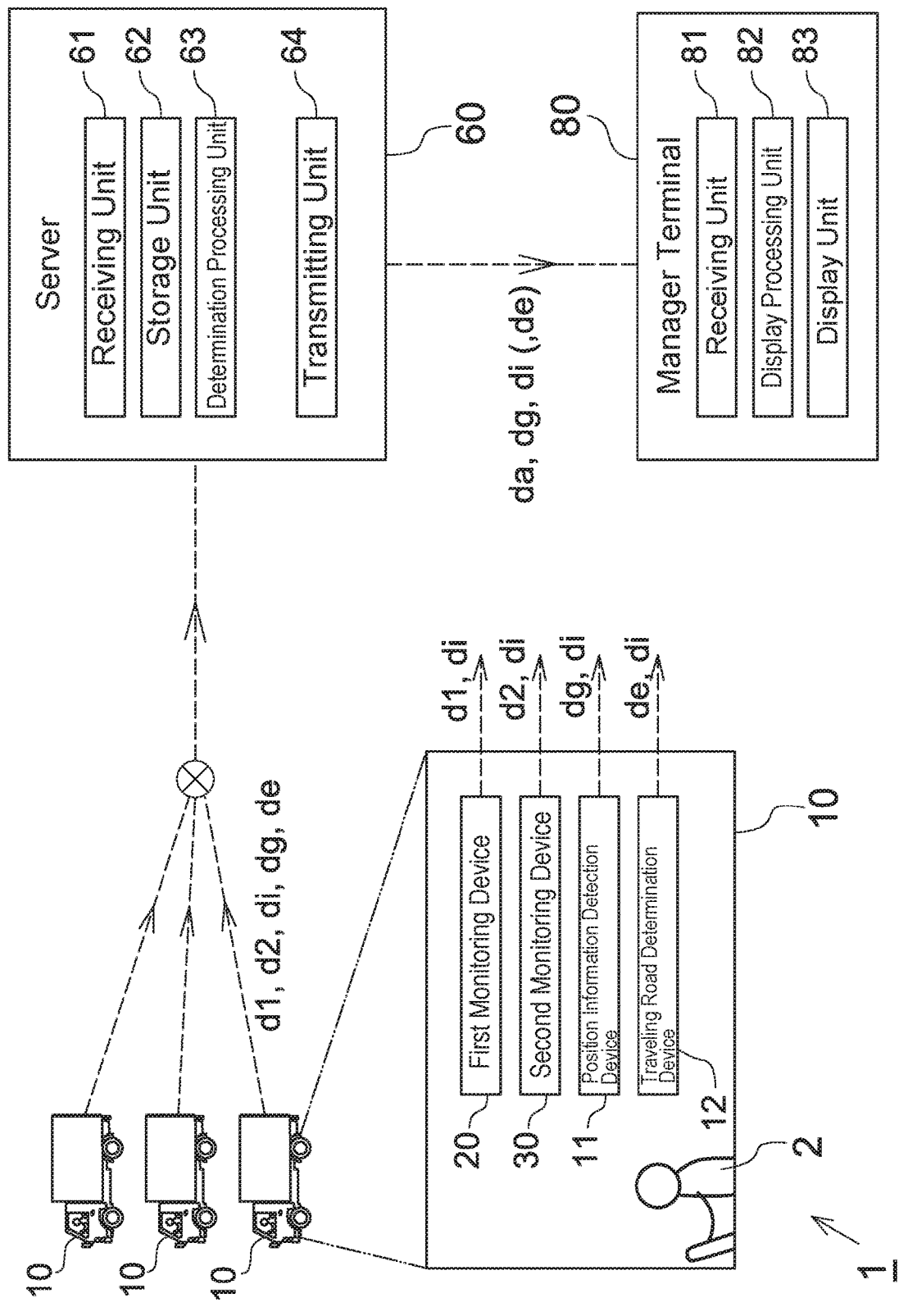
FIG. 11 is another block diagram schematically showing the configuration of the first embodiment of the management assistance system according to the present invention.

(2) Furthermore, as shown in FIG. 11, the target vehicle 10 may include a traveling road determination device 12 that detects that the road on which the target vehicle is traveling has been switched between a general road and a highway. In this case, road information de indicating whether the traveling road of the target vehicle 10 at the time point when each monitoring information (d1, d2) is transmitted from each monitoring device (20, 30) to the server 60 is a general road or a highway may be transmitted together. The traveling road determination device 12 is configured by, for example, an automatic payment system (ETC) mounted on the target vehicle 10. According to this configuration, the road information de of the target vehicle 10 at the time point when each warning condition is satisfied can be stored in the storage unit 62 of the server 60 in association with each monitoring information (d1, d2).

The road information de may be transmitted from the traveling road determination device 12 to each monitoring device (20, 30), and then transmitted from each monitoring device (20, 30) to the server 60 together with each monitoring information (d1, d2). Furthermore, as another method, at the time point when each monitoring information (d1, d2) is transmitted from each monitoring device (20, 30) to the server 60, the road information de may be transmitted from the traveling road determination device 12 to the server 60.

Furthermore, as another method, the traveling road determination device 12 may be configured to periodically transmit, to the server 60, the road information de at a prescribed time interval. In this case, the server 60 may store the road information de in the storage unit 62 and also read out the road information de transmitted at the closest time from the storage unit 62 at a time point when the server receives each monitoring information (d1, d2) transmitted from each monitoring device (20, 30).

The storage unit 62 of the server 60 stores the monitoring-required determination condition in advance depending on whether the road on which the target vehicle 10 travels is a general road or a highway. For example, in the conditions illustrated in FIG. 6, depending on whether the road on which the target vehicle 10 travels is a general road or a highway, the monitoring target occurrence time interval, the number of occurrence threshold value, and/or the condition of combination of the first monitoring information d1 and the second monitoring information d2 can be differed. As a result, the accuracy of determining whether or not the driving situation of the driver 2 is highly dangerous is further enhanced based on the monitoring-required determination conditions suitable for the characteristics of the road on which the target vehicle 10 travels. In this case, in step S33, the server 60 may transmit the road information de together with the monitoring-required notification information da to the manager terminal 80.

In the example shown in FIG. 11, a case in which the target vehicle 10 includes the traveling road determination device 12 and the position information detection device 11 has been described, but the position information detection device 11 may be omitted.

Second Embodiment

Figure 12:
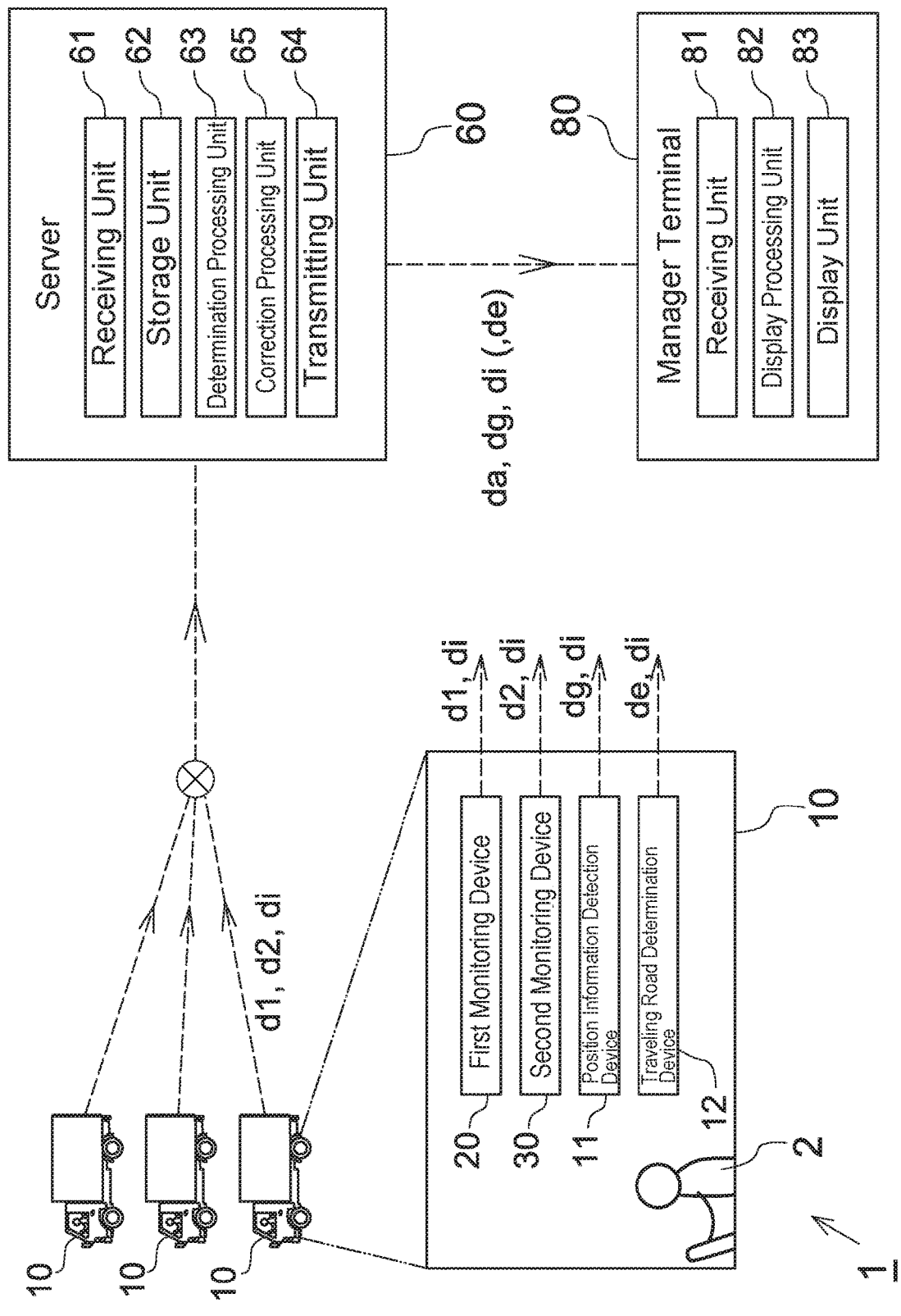
FIG. 12 is a block diagram schematically showing a configuration of a second embodiment of the management assistance system of the present invention.

In a second embodiment of the management assistance system according to the present invention, the points different from the first embodiment will be mainly described. FIG. 12 is a block diagram schematically showing the overall configuration of the management assistance system according to the present embodiment. The management assistance system 1 of the present embodiment is different in that the server 60 includes a correction processing unit 65. The correction processing unit 65 is a calculation processing unit that performs prescribed signal processing (calculation) based on the acquired information, and is configured by dedicated software and/or hardware.

Note that the management assistance system 1 shown in FIG. 12 is shown for a case where the target vehicle 10 includes the position information detection device 11 and the traveling road determination device 12, but these devices (11, 12) may be omitted.

In the present embodiment, the driver 2 performs a process of acquiring information on the physical state (pre-driving physical state) before driving the target vehicle 10. For such information, for example, the body temperature, blood pressure, autonomic nerve, pulse wave, heart rate, blood oxygen concentration, and the like of the driver 2 can be used. Hereinafter, a device for measuring the pre-driving physical state of the driver 2 is referred to as "pre-driving physical state measuring device". The pre-driving physical state measuring device may be permanently installed in a business office where the target vehicle 10 is parked, or may be mounted on each target vehicle 10. Furthermore, the pre-driving physical state measuring device may be a single device or a plurality of device groups.

The pre-driving physical state measuring device measures various biological signals of the driver 2 before driving, and transmits the biological signals to the server 60. The server 60 causes the storage unit 62 to store therein the various biological signals of the driver 2 before driving. That is, the pre-driving physical state measuring device is configured to wirelessly communicate with the server 60. Note that as long as at least the various biological signals measured by the pre-driving physical state measuring device can be transmitted to the server 60, the pre-driving physical state measuring device may not necessarily include a communication means.

Various biological signals of the driver 2 in the past are stored in the storage unit 62 of the server 60. Furthermore, various biological signals of the driver 2 before and after driving in the past or the tendency of the biological signals may be stored. The correction processing unit 65 reads various biological signals of the driver 2 from the storage unit 62 and determines the physical state of the driver 2 at the current time point (hereinafter, referred to as "pre-driving physical state"). For example, if the body temperature of the driver 2 transmitted before driving is higher than the past average body temperature of the driver 2 by greater than or equal to 2° C., determination is made that the pre-driving physical state of the driver 2 is a caution state. Furthermore, as another example, the state of the autonomic nerves of the driver 2 transmitted before driving is evaluated based on the conditions in the table shown in FIG. 13, and whether or not the pre-driving physical state of the driver 2 is a caution state is determined. As still another example, the tendency of the biological signal after driving is predicted from the biological signal before driving, and whether or not the pre-driving physical state is a caution state is determined.

In FIG. 13, "LF" corresponds to an index reflecting the sympathetic nerve, and "HF" corresponds to an index reflecting the parasympathetic nerve. A deviation value Ti is a value obtained by converting a value (ccvTP) in which a value (TP) indicating the function of the entire autonomic nerve function is corrected with the heart rate into a deviation value according to the age of the driver 2. Each of the values of LF, HF, and the deviation value Ti shown in FIG. 13 can be calculated through a calculation process by the correction processing unit 65 based on the values of biological signals such as the pulse wave and heartbeat of the driver 2 measured by the pre-driving physical state measuring device. It should be noted that the storage unit 62 of the server 60 may store information regarding the age of each driver 2.

For example, when determining that the pre-driving physical state of the driver 2 is "caution", the correction processing unit 65 corrects the monitoring-required determination condition of the driver 2 stored in the storage unit 62. As an example, as shown in FIG. 14, the following condition 5 is added to the example of FIG. 6.

(5) Condition 5: One of the following conditions is satisfied. The values $n_2$, and $n_3$ are appropriately set according to the past tendency of the driver 2, and the like.

The server 60 has received the first monitoring information d1 indicating the determination value 1-1, 1-2, 1-3, 1-4, 1-5, or 1-6 $n_1$ or more times within the past 10 minutes including the current time.

The server 60 has received the first monitoring information d1 indicating the determination value 2-2 or 2-3 $n_2$ or more times within the past 10 minutes including the current time.

The server 60 has received the second monitoring information d2 indicating the determination value 3-5, 3-6, 3-7, or 3-8 $n_3$ or more times within the past 10 minutes including the current time.

With the addition of condition 5, the "monitoring-required determination condition", which becomes a reference when the determination processing unit 63 makes a determination, becomes stricter. That is, when the server 60 receives the monitoring information (d1, d2) transmitted from the monitoring devices (20, 30), the probability of determining YES in step S32 increases. In other words, the conditions under which the monitoring-required notification information da is transmitted to the manager terminal 80 are stricter, and the manager can manage in a more concentrating manner the driver 2 whose pre-driving physical state is determined to be caution.

Each value of $n_1$, $n_2$, and $n_3$ in FIG. 14 may be appropriately set according to the pre-driving physical state of the driver 2, or may be a prescribed specified value.

Another Embodiment

Hereinafter, another embodiment will be described.

<1> The determination processing unit 63 of the server 60 may create monitoring-required proximity information indicating the extent the driving situation of the driver 2 has approached the monitoring-required level, based on the monitoring information (d1, d2) transmitted from each monitoring device (20, 30). For example, in the storage unit 62 of the server 60, the fact that the first monitoring information d1 corresponding to any of the determination values 1-1, 1-2, 1-5 has been received 22 times in the past 20 minutes from the target vehicle 10 driven by the driver 2 is stored. In this case, the determination processing unit 63 of the server 60 recognizes that if the equivalent first monitoring information d1 is received eight times over the next 10 minutes, the driving situation of the driver 2 reaches the monitoring-required level.

Figure 15:
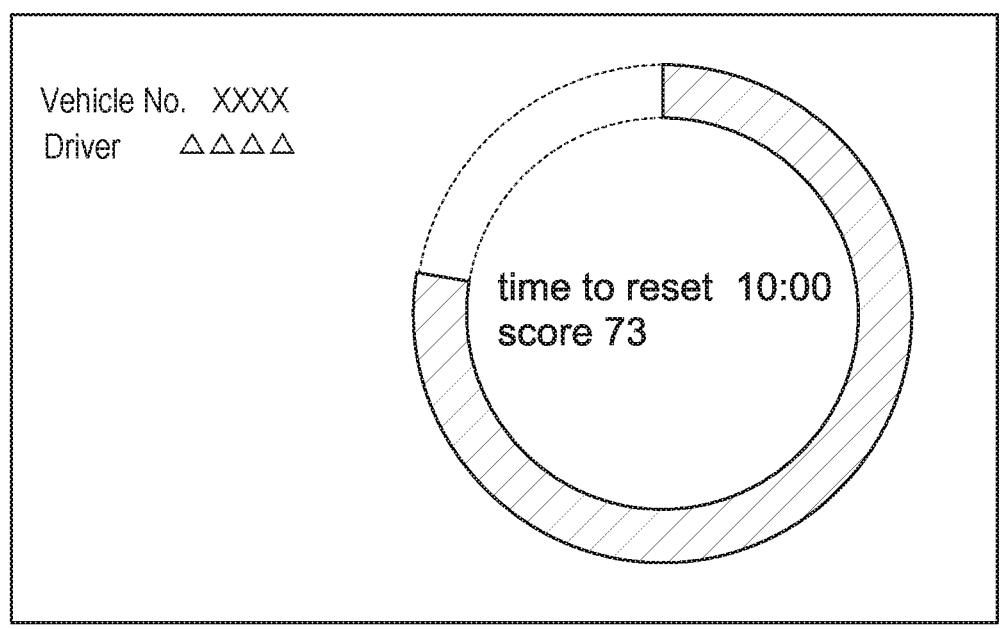
FIG. 15 is an example of an image of monitoring-required proximity information notified to the driver.

In such a case, for example, the server 60 may display information in which the monitoring-required proximity information as shown in FIG. 15 is converted to an image on a screen of a smartphone by transmitting the monitoring-required proximity information to the smartphone owned by the driver 2. In the example of FIG. 15, the evaluation of the driving situation of the driver 2 at the current time point is displayed as a score based on a separation between the number of occurrences according to each monitoring information (d1, d2) and the number of occurrence threshold value defined in advance in the monitoring-required determination condition. In this example, the extent the current number of occurrences is proximate to the threshold value is score displayed assuming a case where the number of occurrences of the target monitoring information (d1, d2) that reached a threshold value within the monitoring target occurrence time interval specified in the monitoring-required determination condition is score 100.

The driver 2 can visually recognize his/her driving situation at the current time point by checking the image information displayed on the smartphone, for example, while the vehicle is stopped.

<2> In the embodiment described above, each monitoring device (20, 30) has been described as transmitting each warning signal (d1, d2) to the server 60 at the time point of detecting that each warning condition is reached. At this time, each monitoring device (20, 30) may also transmit to the server 60, raw data such as image information related to the acceleration of the target vehicle 10 and the proximity state with a front obstacle (vehicle, pedestrian, etc.) and information related to the pulse wave of the driver 2. Furthermore, even if each warning condition is not reached, the information detected by each monitoring device (20, 30) may be periodically transmitted to the server 60.

Thus, information related to the travel state and physical state of the driver 2 in normal times is accumulated in the storage unit 62 of the server 60, so that a monitoring-required determination condition that takes into consideration the characteristics of each driver 2 can be set, and the accuracy in determining whether or not the driving situation of the driver 2 is highly dangerous is further enhanced.

<3> The first monitoring device 20 and/or the second monitoring device 30 may each be configured to include two or more types of devices. For example, the means (transmitting units 24, 34) for realizing wireless communication in each monitoring device (20, 30) may be configured by a terminal device for wireless communication (e.g., a smartphone or a personal computer). Of course, similar replacement/change can be made to other configurations.

<4> Each of the warning conditions and monitoring-required determination conditions described above are merely examples, and the present invention is not limited to these contents. For example, when the first monitoring device 20 mounted on the target vehicle 10 includes a speed sensor and the speed sensor detects that the speed of the target vehicle 10 is traveling at an extremely dangerous high speed, information indicating the same is transmitted to the server 60, and the monitoring-required notification information is immediately notified from the server 60 to the manager terminal 80. Furthermore, as another example, in the target vehicle 10, a time measuring device for measuring the continuous traveling time of the target vehicle 10 is provided, and when the time measuring device detects that the vehicle is continuously traveling for a prescribed time or longer, information indicating the same is transmitted to the server 60, and the monitoring-required notification information is immediately notified from the server 60 to the manager terminal 80.

<5> In the embodiment described above, the first monitoring device 20 and the second monitoring device 30 have been described as outputting warning signals in the target vehicle 10 when detecting that the warning conditions have been reached. However, in the present invention, the first monitoring device 20 and the second monitoring device 30 merely needs to be configured to be able to output the warning signal in the target vehicle 10, and may not necessarily actually output the warning signal.

<6> The present invention is not limited to the embodiments described above, and includes various modifications. For example, the embodiments described above have been described in detail for better understanding of the present invention, and are not necessarily limited to those including all configurations of the description. The scope of the present invention is defined by the Claims, and it is intended to include meanings equivalent to the Claims and all modifications within the scope.

DESCRIPTION OF REFERENCE SIGNS

1 management assistance system
2 driver
10 target vehicle
11 position information detection device
12 traveling road determination device
20 first monitoring device
21 detection unit
22 determination unit
23 warning output unit
24 transmitting unit
30 second monitoring device
31 detection unit
32 determination unit
33 warning output unit
34 transmitting unit
60 server
61 receiving unit
62 storage unit
63 determination processing unit
64 transmitting unit
65 correction processing unit
80 manager terminal
81 receiving unit
82 display processing unit
83 display unit
88 message display region
89 operation region
89a, 89b operation button
d1 first monitoring information
d2 second monitoring information
da monitoring-required notification information
de road information
dg position information
di identification information

The invention claimed is:

1. A management assistance system that assists management of a driving situation of a driver who drives a target vehicle, the management assistance system comprising:
a first monitoring device that is mounted on the target vehicle to monitor a travel state of the target vehicle;
a second monitoring device that is mounted on the target vehicle to monitor a physical state during driving of the driver;
a server configured to wirelessly communicate with the first monitoring device and the second monitoring device; and
a manager terminal configured to wirelessly communicate with the server,
wherein when the travel state satisfies a prescribed first warning condition, the first monitoring device outputs a first warning signal to the driver of the target vehicle and transmits first monitoring information corresponding to the travel state to the server together with identification information for identifying the target vehicle or the driver serving as a transmitting source,
wherein when the physical state during driving satisfies a prescribed second warning condition, the second monitoring device outputs a second warning signal to the driver of the target vehicle and transmits second monitoring information corresponding to the physical state during driving to the server together with the identification information, and
wherein the server includes,
a receiving unit that is configured to receive the first monitoring information transmitted from the first monitoring device and the second monitoring information transmitted from the second monitoring device,
a storage unit that is configured to store a monitoring-required determination condition for determining whether or not a driving situation of the driver reaches a monitoring-required level,
a determination processing unit that is configured to:
in response to the receiving unit receiving only both the first and second monitoring information, determine whether or not the monitoring-required determination condition is satisfied based on the first monitoring information and the second monitoring information received by the receiving unit,
in response to the receiving unit receiving only one of the first or second monitoring information, not determine whether or not the monitoring-required determination condition is satisfied, and
in response to the receiving unit receiving none of the first or second monitoring information, not determine whether or not the monitoring-required determination condition is satisfied, and
a transmitting unit that, when the determination processing unit determines that the monitoring-required determination condition is satisfied, transmits monitoring-required notification information indicating that the driving situation of the driver reaches the monitoring-required level to the manager terminal together with the identification information.

2. The management assistance system according to claim 1, wherein
the first monitoring information includes information converted into numerical values according to risk degree of the travel state;
the second monitoring information includes information converted into numerical values according to non-awakening degree of the driver;

when receiving the first monitoring information and the second monitoring information, the receiving unit stores the identification information corresponding to transmitting source, time information related to received date and time, the first monitoring information and the second monitoring information in the storage unit;

the monitoring-required determination condition includes information related to monitoring target occurrence time interval and number of occurrence threshold value defined according to the risk and the non-awakening degree; and the determination processing unit determines that the monitoring-required determination condition is satisfied when the number of occurrences of the risk described in the first monitoring information or the non-awakening degree described in the second monitoring information within the monitoring target occurrence time interval exceeds the number of occurrence threshold value based on the first monitoring information, the second monitoring information, and the time information stored in the storage unit.

3. The management assistance system according to claim 2, wherein the first monitoring device detects at least one of a separation distance between the target vehicle and a front obstacle located in front of the target vehicle, whether the target vehicle departed from a lane in which the target vehicle is traveling, and an acceleration of the target vehicle, determines the risk degree in advance based on the detection result; and the second monitoring device detects at least one of a heartbeat and a pulse wave of the driver, and determines the non-awakening degree set in advanced based on the detection result.

4. The management assistance system according to claim 1, wherein the identification information is information for identifying the driver, and the storage unit stores the monitoring-required determination condition that is set for each of the drivers identified by the identification information.

5. The management assistance system according to claim 4, wherein the storage unit stores information on a pre-driving physical state, which is a physical state before driving the target vehicle, of the driver, in association with the identification information; and the server includes a correction processing unit that corrects the monitoring-required determination condition based on the pre-driving physical state for each driver.

6. The management assistance system according to claim 1, further comprising, a traveling road determination device that is mounted on the target vehicle and that, at a time point where a road on which the target vehicle is traveling is changed from a general road to a highway and a time point where the road is changed from a highway to a general road, transmits information indicating the change to the server together with the information related to the changed time; and the storage unit stores the monitoring-required determination condition that differs depending on whether the road on which the target vehicle is travelling is the general road or the highway.

7. The management assistance system according to claim 1, further comprising a position information detection device that is mounted on the target vehicle and that detects current position information of the target vehicle and transmits the position information to the server, wherein when the first monitoring information or the second monitoring information is received by the receiving unit, the server stores the position information of the target vehicle at the time of reception in the storage unit together with each monitoring information, and when the determination processing unit determines that the monitoring-required determination condition is satisfied, the transmitting unit transmits the monitoring-required notification information to the manager terminal together with the identification information and the position information.

8. The management assistance system according to claim 2, wherein the storage unit stores the monitoring-required determination condition corresponding to the identification information.

9. The management assistance system according to claim 3, wherein the storage unit stores the monitoring-required determination condition corresponding to the identification information.

10. The management assistance system according to claim 8, wherein the storage unit stores information on a pre-driving physical state, which is a physical state before driving the target vehicle, of the driver, in association with the identification information; and the server includes a correction processing unit that corrects the monitoring-required determination condition based on the pre-driving physical state for each driver.

11. The management assistance system according to claim 9, wherein the storage unit stores information on a pre-driving physical state, which is a physical state before driving the target vehicle, of the driver, in association with the identification information; and the server includes a correction processing unit that corrects the monitoring-required determination condition based on the pre-driving physical state for each driver.

12. The management assistance system according to claim 2, further comprising, a traveling road determination device that is mounted on the target vehicle and that, at a time point where a road on which the target vehicle is traveling is changed from a general road to a highway and a time point where the road is changed from a highway to a general road, transmits information indicating the change to the server together with the information related to the changed time; and the storage unit stores the monitoring-required determination condition that differs depending on whether the road on which the target vehicle is travelling is the general road or the highway.

13. The management assistance system according to claim 3, further comprising, a traveling road determination device that is mounted on the target vehicle and that, at a time point where a road on which the target vehicle is traveling is changed from a general road to a highway and a time point where the road is changed from a highway to a general road, transmits information indicating the change to the server together with the information related to the changed time; and the storage unit stores the monitoring-required determination condition that differs depending on whether the road on which the target vehicle is travelling is the general road or the highway.

14. The management assistance system according to claim 4, further comprising,
    a traveling road determination device that is mounted on the target vehicle and that, at a time point where a road on which the target vehicle is traveling is changed from a general road to a highway and a time point where the road is changed from a highway to a general road, transmits information indicating the change to the server together with the information related to the changed time; and
    the storage unit stores the monitoring-required determination condition that differs depending on whether the road on which the target vehicle is travelling is the general road or the highway.

15. The management assistance system according to claim 2, further comprising
    a position information detection device that is mounted on the target vehicle and that
    detects current position information of the target vehicle and transmits the position information to the server,
    wherein
    when the first monitoring information or the second monitoring information is received by the receiving unit, the server stores the position information of the target vehicle at the time of reception in the storage unit together with each monitoring information, and
    when the determination processing unit determines that the monitoring-required determination condition is satisfied, the transmitting unit transmits the monitoring-required notification information to the manager terminal together with the identification information and the position information.

16. The management assistance system according to claim 3, further comprising
    a position information detection device that is mounted on the target vehicle and that detects current position information of the target vehicle and transmits the position information to the server,
    wherein
    when the first monitoring information or the second monitoring information is received by the receiving unit, the server stores the position information of the target vehicle at the time of reception in the storage unit together with each monitoring information, and
    when the determination processing unit determines that the monitoring-required determination condition is satisfied, the transmitting unit transmits the monitoring-required notification information to the manager terminal together with the identification information and the position information.

17. The management assistance system according to claim 4, further comprising
    a position information detection device that is mounted on the target vehicle and that detects current position information of the target vehicle and transmits the position information to the server,
    wherein
    when the first monitoring information or the second monitoring information is received by the receiving unit, the server stores the position information of the target vehicle at the time of reception in the storage unit together with each monitoring information, and
    when the determination processing unit determines that the monitoring-required determination condition is satisfied, the transmitting unit transmits the monitoring-required notification information to the manager terminal together with the identification information and the position information.

18. The management assistance system according to claim 4, wherein
    the monitoring-required determination condition is set for each of the drivers identified by the identification information by changing the monitoring target occurrence time interval and/or the number of occurrence threshold value.

19. The management assistance system according to claim 4, wherein
    the monitoring-required determination condition is set for each of the drivers identified by the identification information by changing a condition of combination of the first monitoring information and the second monitoring information.

20. The management assistance system according to claim 1, wherein the determination processing unit is configured to:
    in response to a determination that the monitoring-required determination condition is satisfied, generate an indication for the manager terminal to contact the driver of the target vehicle, and
    in response to the receiving unit receiving only one of the first or second monitoring information or none of the first or second monitoring information, not generate the indication for the manager terminal to contact the driver of the target vehicle,
    wherein the first or second warning signal is output to the driver of the target vehicle in response to satisfying the first or second warning condition, and
    wherein selective transmission of the indication for the manager terminal to contact the driver of the target vehicle helps a user of the manager terminal to monitor driving behavior of a fleet of drivers.

* * * * *